United States Patent
Tang et al.

(10) Patent No.: US 10,577,608 B2
(45) Date of Patent: Mar. 3, 2020

(54) METHODS OF USING MICRORNA-199A

(71) Applicants: Dean Tang, Williamsville, NY (US); Ruifang Liu, Buffalo, NY (US)

(72) Inventors: Dean Tang, Williamsville, NY (US); Ruifang Liu, Buffalo, NY (US)

(73) Assignee: Stemirna Therapeutics Co., Ltd., Shanghai (CN)

( * ) Notice: Subject to any disclaimer, the term of this patent is extended or adjusted under 35 U.S.C. 154(b) by 0 days.

(21) Appl. No.: 15/606,592

(22) Filed: May 26, 2017

(65) Prior Publication Data
US 2017/0342421 A1    Nov. 30, 2017

Related U.S. Application Data

(60) Provisional application No. 62/341,636, filed on May 26, 2016.

(51) Int. Cl.
*C12N 15/113* (2010.01)
*C12N 5/00* (2006.01)

(52) U.S. Cl.
CPC .... *C12N 15/1138* (2013.01); *C12N 2310/141* (2013.01); *C12N 2320/30* (2013.01)

(58) Field of Classification Search
None
See application file for complete search history.

(56) References Cited

PUBLICATIONS

Kreso and Dick. Evolution of the cancer stem cell model. Cell Stem Cell 2014; 14 (3):275-91.
Tang DG. Understanding cancer stem cell heterogeneity and plasticity. Cell Res 2012; 22 (3):457-72.
Leung et al. Non-small cell lung cancer cells expressing CD44 are enriched for stem cell-like properties. PLoS ONE 2010; 5 (11):e14062.
Su et al. Direct reprogramming of stem cell properties in colon cancer cells by CD44. EMBO J 2011; 30 (15):3186-99.
Du et al. CD44-positive cancer stem cells expressing cellular prion protein contribute to metastatic capacity in colorectal cancer. Cancer Res 2013; 73 (8):2682-94.
Patrawala et al. Highly purified CD44+ prostate cancer cells from xenograft human tumors are enriched in tumorigenic and metastatic progenitor cells. Oncogene 2006; 25 (12):1696-708.
Patrawala et al. Hierarchical organization of prostate cancer cells in xenograft tumors: the CD44+alpha2beta1+ cell population is enriched in tumor-initiating cells. Cancer Res 2007; 67 (14):6796-805.
Qin et al. The PSA(-/lo) prostate cancer cell population harbors self-renewing long-term tumor-propagating cells that resist castration. Cell Stem Cell 2012;10 (5):556-69.
Liu et al. The microRNA miR-34a inhibits prostate cancer stem cells and metastasis by directly repressing CD44. Nat Med 2011;17 (2):211-5.
Liu et al. Systematic dissection of phenotypic, functional, and tumorigenic heterogeneity of human prostate cancer cells. Oncotarget 2015; 6 (27): 23959-86.
Ha and Kim. Regulation of microRNA biogenesis. Nat Rev Mol Cell Biol 2014;15 (8):509-24.
Ling et al. MicroRNAs and other non-coding RNAs as targets for anticancer drug development. Nat Rev Drug Discov 2013;12 (11):847-65.
Liu et al. Role of microRNAs in the regulation of breast cancer stem cells. J Mammary Gland Biol Neoplasia 2012; 17 (1):15-21.
Liu and Tang. MicroRNA regulation of cancer stem cells. Cancer Res 2011; 71(18):5950-4.
Liu C et al. Distinct microRNA expression profiles in prostate cancer stem/progenitor cells and tumor-suppressive functions of let-7. Cancer Res 2012; 72(13): 3393-404.
Hayes et al. MicroRNAs in cancer: biomarkers, functions and therapy. Trends Mol Med 2014; 20(8):460-9.
Qu et al. miR-199a-3p inhibits aurora kinase A and attenuates prostate cancer growth: new avenue for prostate cancer treatment. Am J Pathol 2014;184 (5):1541-9.
Li et al. Methodologies in assaying prostate cancer stem cells. Methods Mol Biol 2009; 568: 85-138.
Li et al. PC3 human prostate carcinoma cell holoclones contain self-renewing tumor-initiating cells. Cancer Res 2008; 68 (6):1820-5.
Jeter et al. Functional evidence that the self-renewal gene NANOG regulates human tumor development. Stem Cells 2009; 27 (5):993-1005.
Goldstein et al. Purification and direct transformation of epithelial progenitor cells from primary human prostate. Nat Protoc 2011; 6 (5):656-67.
Liu et al. Down-regulation of miR-517a and miR-517c promotes proliferation of hepatocellular carcinoma cells via targeting Pyk2. Cancer Lett 2013; 329 (2):164-73.
Hou et al. Identification of miRNomes in human liver and hepatocellular carcinoma reveals miR-199a/b-3p as therapeutic target for hepatocellular carcinoma. Cancer Cell 2011;19 (2):232-43.
Henry et al. miR-199a-3p targets CD44 and reduces proliferation of CD44 positive hepatocellular carcinoma cell lines. Biochem Biophys Res Commun 2010; 403 (1):120-25.
Fornari et al. MiR-199a-3p regulates mTOR and c-Met to influence the doxorubicin sensitivity of human hepatocarcinoma cells. Cancer Res 2010; 70 (12):5184-93.
Kim et al. MicroRNA miR-199a regulates the MET proto-oncogene and the downstream extracellular signal-regulated kinase 2 (ERK2). J Biol Chem 2008; 283 (26):18158-66.
Duan et al. MicroRNA-199a-3p is downregulated in human osteosarcoma and regulates cell proliferation and migration. Mol Cancer Ther 2011;10 (8):1337-45.
Kinose et al. The hypoxia-related microRNA miR-199a-3p displays tumor suppressor functions in ovarian carcinoma. Oncotarget 2015; 6 (13):11342-56.

(Continued)

*Primary Examiner* — Sean McGarry
(74) *Attorney, Agent, or Firm* — Benjamin Aaron Adler

(57) ABSTRACT

Provided herein are methods of treating a cancer in an individual. A microRNA-199a oligonucleotide or mimic that increases the expression of microRNA-199a in the cancer cell is administered to the individual. Also provided is a method of inhibiting proliferation of a cancer cell and treating a cell associated with a cancer. The cell is contacted with the microRNA-199a oligonucleotide or mimic.

7 Claims, 26 Drawing Sheets
Specification includes a Sequence Listing.

(56) References Cited

PUBLICATIONS

Minna et al. miR-199a-3p displays tumor suppressor functions in papillary thyroid carcinoma. Oncotarget 2014; 5 (9):2513-28.
Goldstein et al. Identification of a cell of origin for human prostate cancer. Science 2010; 329 (5991):568-71.
Saini et al. miRNA-708 control of CD44(+) prostate cancer-initiating cells. Cancer Res 2012;72 (14):3618-30.
Dang CV. MYC, metabolism, cell growth, and tumorigenesis. Cold Spring Harb Perspect Med 2013; 3(8) 1-15.
Koh et al. MYC and Prostate Cancer. Genes Cancer 2010;1 (6):617-28.
Gil et al. Immortalization of primary human prostate epithelial cells by c-Myc. Cancer Res 2005; 65(6):2179-85.
Civenni et al. RNAi-mediated silencing of Myc transcription inhibits stem-like cell maintenance and tumorigenicity in prostate cancer. Cancer Res 2013;73 (22):6816-27.
Ding et al. SMAD4-dependent barrier constrains prostate cancer growth and metastatic progression. Nature 2011;470 (7333):269-73.
Ju et al. Identification of a cyclin D1 network in prostate cancer that antagonizes epithelial-mesenchymal restraint. Cancer Res 2014;74 (2):508-19.
Chang et al. EGF Receptor Promotes Prostate Cancer Bone Metastasis by Downregulating miR-1 and Activating TWIST1. Cancer Res 2015.
Asangani et al. Therapeutic targeting of BET bromodomain proteins in castration-resistant prostate cancer. Nature 2014; 510 (7504):278-82.
Chang et al. Widespread microRNA repression by Myc contributes to tumorigenesis. Nat Genet 2008 ;40 (1):43-50.

Inserted sequence in lentivirus (pGIPZ-199A and lenti-199A): (SEQ ID NO: 1)

5'- CAGCTAATGCCACATCTGAGCTGAACTGTTTACAGTGCAATTCCGCGCGAGAAATCAGTGGCCGCCTTCCT
GGTGCTGCGGCACGCGTGCGCGTGCGCGGCGCACACACACGTGTGTGCGCC
CCTCCTCCCCAGACCCCGCCCCACAGAGTCAGACATTCCTGAGCCAAGCCACGATCCC
AAACCCTGCCTCGCTCCGCGCCTCCCCACTCTTTAGGATTTCCTGAAAACCCAGAACTTTCTCCA
GATGCCAGCGGCCCAGCCCTTGCCACGTCAGAGGACAGAGAGCGGATCGTCTCGGGAAGAGTG
GTGGTTTCCTTGGCTGCTCAGAGGTGCTGACGCGGCACGGCTGGTGGCCCCAGGCGTCTGCC
TGGGGGGTCTGCAGGATGGCAGCGGCCCGACAGCCAGTGCAGACGTTCAGAGTTCAAGGAG
                                          pre-miR-199A1
GCGTCTCAAGTGTACAGTAGTCTGCACATTGGTTAGGCTGGGGCTTGAGGGCTCGTGTGAGAC
              hsa-miR-199a-3p
AGGCCCCCAAACTCGCGGCAGGTGAGTGTCATTTCCACCACCGTTCCCACTGTGGCAGA
GCCTCGCATAGAAGATTCGAGGCCGGCCTGGAAGAGCCACTGGGAAAGGCACTGAGAGGAGC
CCCGAGGCCGGCCGGAGGGGTTGGAGGCCTGGAGGCCTGGCCTATCAGTCTGCCATCCCCACCCCATGGCT
GTAAATGTCTTGTTTATTTTTAAATAAAGAGATATTGATGTCTTGTGTCTCACTGAGCCATCTAAGAG
GGTGGCCTCCTCCTCAGGGGGTGCCCTCGTGTGCACGTGTGTGACTCGTGTGCCAAGGGTCCCTGCTGGGATCCTA
ACTTGG-3'

| | Forword Primer (SEQ ID NO: 2) | Reverse Primer (SEQ ID NO: 3) |
|---|---|---|
| pGIPZ-199A | (XhoI)TACTCGAGCCAGCTAATGCCACATC | ATACGCGTCCAAGTTAGGATCCCA(MluI) |
| lenti-199A | (ClaI) TAATCGATCAGCTAATGCCACATC | ATACGCGTCCAAGTTAGGATCCCA(MluI) |
| | (SEQ ID NO: 4) | (SEQ ID NO: 5) |

FIG. 1A

| CD44⁺DU145 (100K, s.c., 64d) | Incidence | P Value | Weight (g) | P Value |
|---|---|---|---|---|
| NC | 9/10 (90%) | 0.3049 | 0.856 ± 0.152 | 0.0032 |
| 3p | 10/10 (100%) | | 0.203 ± 0.057 | |
| CD44⁺DU145 (10K, s.c, 94d) | | | | |
| NC | 8/10 (80%) | 0.0246 | 0.421 ± 0.471 | 0.1384 |
| 3p | 3/10 (30%) | | 0.040 ± 0.021 | |

| | | Incidence | P Value | Weight (g) | P Value |
|---|---|---|---|---|---|
| Exp. I | DU145(100K, s.c., 68d) | | | | |
| | NC | 5/6 (83%) | 0.0034 | | |
| | 3p | 0/6 (0%) | | | |
| | DU145(10K, s.c., 68d) | | | | |
| | NC | 4/4 (100%) | 0.0047 | | |
| | 3p | 0/4 (0%) | | | |
| Exp. II | DU145(100K, s.c., 67d) | | | | |
| | NC | 9/10 (90%) | 0.0191 | 0.171±0.085 | 0.0047 |
| | 3p | 4/10 (40%) | | 0.057±0.030 | |

DU145 CD44+ Tumor

LAPC9 Tumor

METHODS OF USING MICRORNA-199A

CROSS-REFERENCE TO RELATED APPLICATIONS

This non-provisional application claims benefit of priority under 35 U.S.C. § 119(e) of provisional application U.S. Ser. No. 62/341,636, filed May 26, 2016, the entirety of which is hereby incorporated by reference.

BACKGROUND OF THE INVENTION

Field of the Invention

The present invention relates to the fields of molecular biology and oncology. More specifically, the present invention relates to method involving use of microRNA-199a as tumor suppressors able to significantly suppress cell proliferation and tumor growth.

Description of the Related Art

Human cancers are heterogeneous containing phenotypically differentiated cancer cells as well as immature stem-like cancer cells or cancer stem cells (1,2). CD44, a cell surface adhesion receptor with pleiotropic signaling functions, is highly enriched in and has been used to enrich cancer stem cells in a variety of tumors (3-5). Systematic studies have demonstrated that CD44 is a prostate cancer stem cell enrichment marker that plays a causal role in prostate cancer development and metastasis (6-10). For example, purified $CD44^+$ cell population demonstrates high tumorigenic and metastatic potential (6) and knockdown of CD44 inhibits tumorigenicity and metastasis of prostate cancer cells in multiple models (9). Also, $CD44^+$ cells are relatively quiescent, express high levels of "stemness" genes including Oct-3/4, Bmi, β-catenin and SMO (6). Prostate cancer cells double-positive for CD44 and integrin $\alpha_2\beta_1$ (i.e., $CD44^+\alpha_2\beta_1^+$) are even more tumorigenic than CD44+ prostate cancer cells (7). Finally, it is shown that the $CD44^+$ $\alpha_2\beta_1^+ALDH^+$ subpopulation in the undifferentiated) ($PSA^{-/lo}$) cell pool identifies highly tumorigenic and castration-resistant prostate cancer cells (8). Together, these studies highlight the involvement of $CD44^+$ prostate cancer stem cells in prostate cancer development, metastasis and therapy resistance and suggest that it will be important to understand how prostate cancer stem cells are molecularly regulated.

MicroRNAs (miRNAs), ~22 nucleotides small non-coding RNAs, exert their functions via base-pairing with the target mRNA. Over 60% of human coding genes contain at least one conserved microRNA binding site, and most coding genes in the human genome are probably under the control of microRNAs (11). Dysregulation of microRNA expression and functions has been widely reported and some microRNAs have been explored as anti-cancer therapeutics (12). Nevertheless, microRNA regulation of cancer stem cells in general and prostate cancer stem cells in particular remains incompletely understood. Recent evidence suggests that microRNAs may play important functions in regulating cancer stem cells and tumor development (13,14). Earlier microRNA library screening has identified several microRNAs, i.e., miR-34a, let-7b, miR-141, and miR-106 that are commonly under-expressed in tumorigenic prostate cancer cell subsets including $CD44^+$, $CD133^+$ and $\alpha2\beta1^+$ prostate cancer cells (9,15). Functional interrogations on miR-34a (9) and let-7a (15) revealed prostate tumor- and/or metastasis-suppressive functions for the two microRNAs, which function via different mechanisms. miR-34a is the first microRNA being developed for cancer therapy and is currently in a phase II clinical trial for primary liver cancer (16). Interestingly, miR-199a-3p is one of the microRNAs most dramatically underexpressed in the $CD44^+$ prostate cancer cell populations uncovered in the microRNA library screening (15).

MiR-199a-3p is an under-studied microRNA, especially in prostate cancer, with only one report so far showing miR-199a-3p underexpression in prostate cancer compared to benign tissues (17).

Therefore, it would be beneficial to find evidence for tumor suppressive functions of miR-199a-3p in both purified $CD44^+$ and bulk prostate cancer cells based on in vitro clonogenic and in vivo tumor regeneration assays as well as therapeutic experiments. It is also shown that miR-199a-3p exerts its prostate cancer suppressive functions via targeting CD44 and several mitogenic molecules including c-Myc, cyclin D1 and EGFR. The prior art is deficient in this respect. The present invention fulfills this longstanding need and desire in the art.

SUMMARY OF THE INVENTION

The present invention is directed to a method of treating cancer in an individual. The method comprises administering to the individual a pharmacologically effective amount of a microRNA-199a oligonucleotide or microRNA-199a mimic or a pharmaceutical composition thereof that increases the expression of microRNA-199a in the cell associated with cancer.

The present invention also is directed to a method of inhibiting proliferation of a cell associated with a cancer. The method comprises administering to the individual a pharmacologically effective amount of microRNA-199a oligonucleotide or microRNA-199a mimic or a pharmaceutical composition thereof that increases the expression of microRNA-199a in the cancer cell.

The present invention is directed further to a method of inhibiting proliferation of a cell associated with a cancer. The method comprises contacting the cell with a pharmacologically effective amount of a of a microRNA-199a oligonucleotide or microRNA-199a mimic or a pharmaceutical composition thereof that increases the expression of microRNA-199a in the cell.

Other and further aspects, features, benefits, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

FIGS. 1A-1M represent enforced expression of miR-199a-3p inhibits cell proliferation. FIG. 1A shows the pre-miR-199A1 sequence inserted in either the pGIPZ-199A or lenti-199A lentiviral vectors established in the lab. The PCR primers that harbor the cloning restriction sites are indicated.

FIG. 1B shows Genomic coding locations of miR-199a-3p. miR-199a-3p is derived from either miR-199A1 or miR-199A2, which is encoded from the intronic regions of DNM2 (Chr. 19p) or DNM3 (Chr. 1q), respectively. FIG. 1C shows relative expression levels of miR-199a-3p. CD44+ and CD44− cells were purified from DU145 cultures and two xenografts (LAPC9 and VCaP) and total RNA was used in qPCR. The y-axis represents the miR-199a-3p levels in CD44+ cell population relative to its levels in CD44-population (1). FIGS. 1D-1H show cell viability assays. CD44+ DU145 (D) and PC3 (E) cells, or bulk DU145 (F), PC3 (G), and VCaP cells (H) were transfected with 30 nM of NC or miR-199a-3p oligos and plated (20,000 cells/well) at day 0 and live cells counted at indicated days under microscope. FIGS. 1I-1K show DNA content analysis in bulk PC3 (I) or DU145 (J) PPC-1 (K) cells transfected with miR-199a-3p or neutral control (30 nM, 48 h). Bars represent the average percentage of cells in each cell-cycle phase. FIGS. 1L-1M show BrdU incorporation assays in PC3 and DU145 cells transfected with miR-199a-3p or NC (30 nM, 72 h). All bars and data points represent the mean±S.D from 2-5 independent experiments with each condition having 2-3 replicates in each experiment. *P<0.05, **P<0.01.

FIGS. 2A-2B show holoclone assays in freshly purified CD44+ (A) or bulk DU145 (B) cells. Neutral control or miR-199a-3p transfected cells (numbers indicated) were plated in 6-well plates and holoclones enumerated on day 12 (for A) and 14 (for B), respectively FIGS. 2C-2D show sphere assays in bulk DU145 cells. Cells were plated on 6-well ULA plates (C) or mixed with Matrigel (1:1) before plating (D) and spheres scored on day 13. FIGS. 2E-2G show holoclone and sphere-formation assays in bulk PC3 (E, F) and LAPC9 (G) cells transfected with neutral control or miR-199a-3p. For E, 100 cells were plated and holoclones scored on day 15. For F, primary sphere assays were conducted by plating 2K or 5K cells in ULA plates and spheres scored on day 7. In secondary sphere assays, the first generation spheres were harvested, digested into single cells, and replated at 5K cells, and spheres scored on day 25. For G, 5K cells were plated and spheres scored on day 18. Cells here were transfected with neutral control or miR-199a-3p (3p) oligos at 30 nM. All bars represent the mean±S.D from 2-4 independent experiments with each condition having 3 replicates. *P<0.05, **P<0.01.

FIG. 3A shows matrigel-based sphere assays in HPCa215 cells. 400 cells were plated in triplicate in six-well plate and spheres scored on day 7. FIGS. 3B-3C show matrigel-based sphere (B) and holoclone (C) assays in HPCa216 cells. For B, 500 cells were plated in triplicate and spheres scored on day 7. For C, the indicated number of cells was plated in six-well plate and images taken on day 8. FIGS. 3D-3E show holoclone and Matrigel-based sphere assays in HPCa217 cells. In FIG. 3D, the indicated numbers of cells were plated in six-well plate and images taken on day 8. In FIG. 3E (limiting dilution sphere assays), 500 or 1,000 cells were plated in six-well plates and colonies scored on day 8. FIG. 3F shows holoclone assays in CD44+ cells sorted from HPCa219 patient tumor. 400 TROP2+CD44+ cells (purity 96.7%, below) were plated in triplicate and holoclones scored on day 9. Cells transfected with neutral control or miR-199a-3p (3p) oligos at 30 nM were used in above experiments (n=2-3 for each experiment). All bars and data points represent the mean±S.D; *P<0.05, **P<0.01.

FIG. 4A shows tumor regeneration assays in purified CD44+ DU145 cells, transfected with neutral control or miR-199a-3p (30 nM, 48 h) and s.c. injected, at 2 cell doses, into NOD/SCID mice. Tumor harvest time, weight, incidence and the corresponding P values are indicated. FIG. 4B shows tumor regeneration assays in bulk DU145 cells transfected with neutral control or miR-199a-3p oligos (30 nM, 48 h) and s.c. injected in two independent experiments. FIG. 4C represents Schematic showing miR-199a-3p expressing vector pGIPZ-199A based on GIPZ lentiviral shRNA backbone (pGIPZ-Ctrl). hsa-miR-199A1, human miR-199A1 and its flanking sequences (759 bp), inserted into XhoI and MluI sites. FIGS. 4D-4E show Subcutaneous tumor regeneration from DU145 (D) and LAPC9 (E) cells infected with pGIPZ-199A or pGIPZ-Ctrl lentivirus. DU145 cells were infected with the lentiviruses (MOI=10) followed by puromycin selection for ~2 weeks (D). LAPC9 cells were similarly infected for 48 h without puromycin selection (E). GFP images and bar graphs showed the transduction efficiency of pGIPZ-199A. The relative expression levels of miR-199a-3p and miR-199a-5p were measured by RT-qPCR. Shown in panels b are tumor harvest time, weight, incidence and P values. FIGS. 4F-4G show HE and IHC staining for tumors generated in neutral control or miR-199a-3p transfected CD44+ DU145 (F) and pGIPZ-Ctrl or pGIPZ-199A transduced LAPC9 (G) cells. 4-8 fields were chosen from each slide for counting Ki-67+ cells. Original magnification: 40×, insets: 400×.

FIG. 5A represents schematic of inducible miR-199a-3p expressing lentiviral vector. FIG. 5B shows qPCR analysis of miR-199a-3p after Dox treatment for 72 h (left panel). Images show RFP expression before and after Dox administration (right panel). FIG. 5C shows measurement of tumor volume on the indicated days in lenti-199a (right) and lenti-Ctrl group (left) without or with Dox supplied in the feed on day 25. *P<0.05 between the two groups. FIG. 5D shows HE and Ki-67 staining comparison between the two subgroups, i.e., before and after Dox (original magnification: 150×). Shown on the right is a bar graph presenting Ki-67+ cells (4-8 fields were counted from each slide). *P<0.05.

FIG. 6A represents schematic of the CD44 3'-UTR with several microRNA binding sites indicated. CD44 transcription ID: ENST00000263398. The location of 1521 and 1606 in parenthesis was reported in reference (31). FIG. 6B shows predicted duplex formed between miR-199a-3p and 3'-UTR of CD44 by the RNA22 program. Red lower case letters highlight the mutated nucleotides. FIG. 6C shows luciferase reporter assays documenting the luciferase activities in DU145 and VCaP cells cotransfected with miR-199a-3p/NC oligos with CD44 3'-UTR wild-type (WT) construct or the mutant (MUT). Values represent the mean±SEM (n=4). **P<0.01. FIGS. 6D-6E show mRNA (D) and protein (E) of CD44 in NC or miR-199a-3p transfected DU145 and PC3 cells. FIGS. 6F-6H show IHC staining of CD44 in endpoint tumors. Original magnifications: top panels (80×); bottom panels (400×).

FIG. 7A shows western blotting showing the protein levels of c-MYC in LAPC9, PC3 and DU145 cells transfected with NC or miR-199a-3p (lanes 1-4 and 9-10) or co-transfected with pCDH-Myc vector (lanes 5-6 and 9-10) for 72 h. FIG. 7B shows schematic of the predicted (by RNA22 program) binding site of miR-199a-3p at the CCND1 and EGFR 3'-UTRs or c-MYC CDS. FIG. 7C shows luciferase assays showing the activity of WT or mutant MYC 3'UTR in PC3 cells expressing miR-199a-3p. FIGS. 7D-7E show cell viability of c-MYC siRNAs (20 nM; D) or small molecule inhibitor JQ1 (E) treated PC3 cells, measured by MTT assays. FIG. 7F shows sphere assays in PC3 cells transfected with 3 different c-MYC siRNAs (20 nM). Cells were plated in six-well plate at indicated cell numbers and spheres scored on day 6. FIG. 7G shows WB of cyclin D1 and EGFR in PC3 cells expressing miR-199a-3p (15 nM or 30 nM; 72 h). FIG. 7H shows luciferase assays showing the activity of WT or mutant cyclin D1 or EGFR 3-UTR in PC3 cells expressing miR-199a-3p. FIG. 7I shows mTOR, phosphorylated AKT and AKT were determined by WB in DU145 cells treated with NC or miR-199a-3p (10 nM, 72 h). The expression levels of proteins in FIGS. 7B, 7G and 7I were quantified by densitometry and normalized to the corresponding β-actin levels. Error bars in FIGS. 7C, 7D-F, and 7H represent the SEM of three independent experiments. *$P<0.05$; **$P<0.01$.

DETAILED DESCRIPTION OF THE INVENTION

Figure 1B:
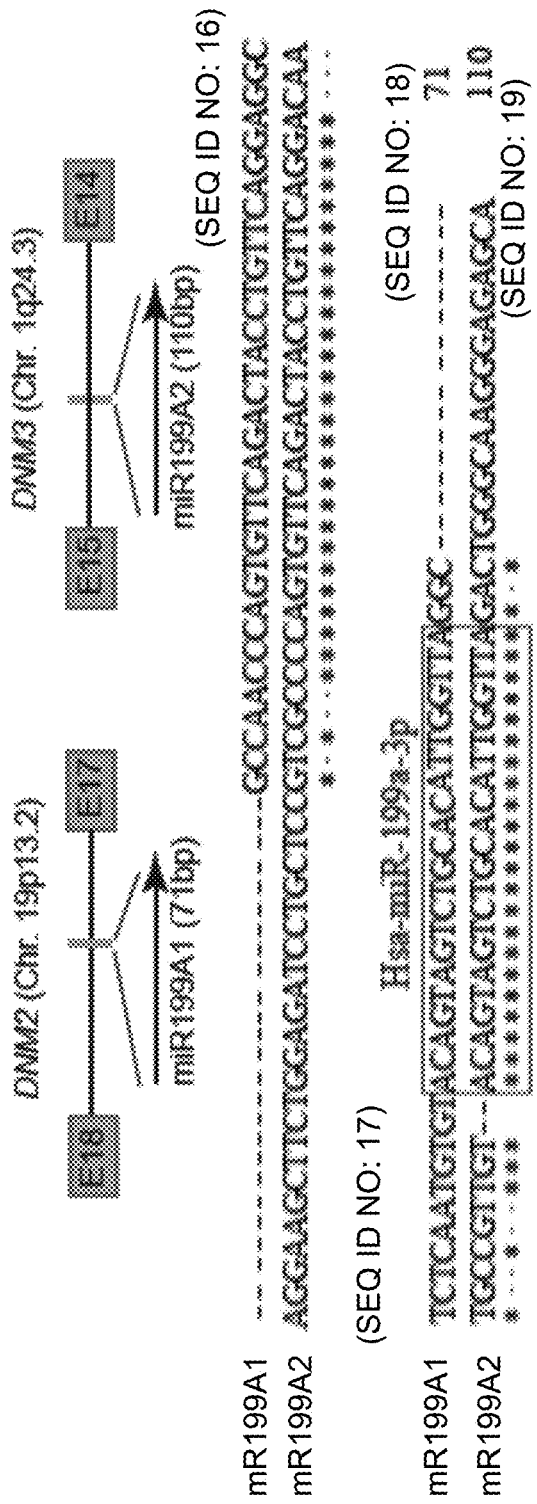

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, "treating" refer to administering to a individual a composition so that the individual has an improvement in the disease or condition. The improvement is any observable or measurable improvement. Thus, one of skill in the art realizes that a treatment may improve the individual's condition, but may not be a complete cure of the disease. Treating may also comprise treating individuals at risk of developing a disease and/or condition of the invention.

As used herein "composition" refers to a pharmaceutical composition comprising the microRNA-199a of the invention and optionally a pharmaceutically acceptable carrier. The compositions may be used for diagnostic or therapeutic applications. The administration of the pharmaceutical composition may be carried out by known methods, wherein a microRNA-199a is introduced into a desired target cell in vitro or in vivo.

As used herein "pharmacologically effective amount" refers to generally an amount effective to accomplish the intended purpose. However, the amount can be less than that amount when a plurality of the compositions are to be administered, i.e., the total effective amount can be administered in cumulative dosage units. The amount of active agent can also be more than the effective amount when the composition provides sustained release of the pharmacologically active agent. The total amount of a pharmacologically active agent to be used can be determined by methods known to those skilled in the art. However, because the compositions may deliver the pharmacologically active agent more efficiently than prior compositions, less amounts of active agent than those used in prior dosage unit forms or delivery systems can be administered to a subject while still achieving the same blood levels and/or therapeutic effects.

As used herein "contacting" refers to any suitable method of bringing a compound or a pharmaceutical composition into contact with a cell in vivo, in vitro or ex vivo. For in vivo applications, any known method of administration is suitable as known in the art.

In one embodiment, there is provided a method of treating cancer in an individual, comprising administering to the individual a pharmacologically effective amount of a microRNA-199a oligonucleotide or microRNA-199a mimic or a pharmaceutical composition thereof that increases the expression of microRNA-199a in the cell of associated with cancer.

In this embodiment the cancer may be prostate, prostate cancer, liver cancer or lung cancer. Also in this embodiment, microRNA-199a is miR-199a-3p or miR-199a-5p. In addition, miR-199a-3p sequence is shown in SEQ ID NO: 22 or SEQ ID NO: 24. Furthermore, the cancer is prostate cancer and administering the microRNA-199a oligonucleotide or microRNA-199a mimic decreases the levels of CD44, c-Myc, cyclin D1, EGFR or mTOR protein in a prostate cancer cell. Further still, administering the microRNA-199a oligonucleotide or microRNA-199a mimic inhibits, cell proliferation, invasion, migration, tumor growth, tumor regeneration, or metastatic potential or a combination thereof.

In another embodiment, there is a method of inhibiting proliferation of a cancer cell in an individual comprising administering to the individual a pharmacologically effective amount of microRNA-199a oligonucleotide or microRNA-199a mimic or a pharmaceutical composition thereof that increases the expression of microRNA-199a in the cancer cell.

In this embodiment the cancer may be prostate, prostate cancer, liver cancer or lung cancer. Also in this embodiment, microRNA-199a is miR-199a-3p or miR-199a-5p. In addition, miR-199a-3p sequence is shown SEQ ID NO: 22 or SEQ ID NO: 24. Furthermore, administering the microRNA-199a oligonucleotide or microRNA-199a mimic inhibits invasion, migration, tumor growth, tumor regeneration, or metastatic potential of the cancer cell. Further still, the cancer is prostate cancer and administering the microRNA-199a oligonucleotide or microRNA-199a mimic decreases the levels of CD44, c-Myc, cyclin D1, EGFR or mTOR protein in a prostate cancer cell.

In yet another embodiment, there is provided A method of inhibiting proliferation of a cell associated with a cancer, comprising contacting the cell with a pharmacologically effective amount of a of a microRNA-199a oligonucleotide or microRNA-199a mimic or a pharmaceutical composition thereof that increases the expression of microRNA-199a in the cell.

In this embodiment the cancer may be prostate, prostate cancer, liver cancer or lung cancer. Also in this embodiment, microRNA-199a is miR-199a-3p or miR-199a-5p. In addition, miR-199a-3p sequence is shown SEQ ID NO: 22 or SEQ ID NO: 24. Furthermore, the cancer is prostate cancer and contacting the cell with the microRNA-199a oligonucleotide or microRNA-199a mimic decreases the levels of CD44, c-Myc, cyclin D1, EGFR or mTOR protein in a prostate cancer cell. Further still, contacting the cell with the microRNA-199a oligonucleotide or microRNA-199a mimic inhibits, cell proliferation, invasion, migration, tumor growth, tumor regeneration, or metastatic potential or a combination thereof.

The following examples are given for the purpose of illustrating various embodiments of the invention and are not meant to limit the present invention in any fashion.

Example 1

Materials and Methods
Cells, Xenografts, Animals, Reagents and Antibodies

DU145, PC3, and PPC-1 cells were obtained from ATCC (Manassas, Va.) and cultured in RPMI1640 medium whereas LAPC9 and VCaP cells were maintained in xenograft tumors. These cell line and xenograft models have been routinely utilized (6-10,15,18-20) and regularly authenticated by CCSG Cell Line Characterization Core using short tandem repeat (STR) analysis and checked to be free of mycoplasma contamination using the Agilent (Santa Clara, Calif.) MycoSensor QPCR Assay Kit (cat.#302107). NOD/SCID mice are produced mostly from breeding colonies and purchased occasionally from the Jackson Laboratories (Bar Harbor). CD44$^+$ cells were purified either by fluorescence-activated cell sorting (FACS) or magnetic-activated cell sorting (MACS). Antibodies used included FITC- or PE-conjugated mouse anti-human CD44 used in FACS purification of CD44+/hi PCa cells and a rabbit monoclonal ani-CD44 used in WB. Other reagents included FcR (130-059-901, Miltenyi Biotec), anti-FITC microbeads (120-000-293, Miltenyi Biotec) and anti-PE microbeads (120-000-294, Miltenyi Biotec).

Xenograft Tumor and Primary Human Prostate Cancer (HPCa) Processing

Xenograft tumor processing has been described previously (6-10) and detailed in reference. (18). All HPCa samples were obtained with the written informed patients' consent from Da Vinci robotic surgery in accordance with federal and institutional guidelines with the approved IRB protocol (MDACC LAB04-0498) and processed as described (9,20) with minor modifications. Briefly, tumor pieces were trimmed, cut into small chunks and rinsed with cold PBS twice. Tumor pieces were then digested in the order of collagenase/dispase solution (Collagenase, 17018-029, GIBCO, Life Technology; Dispase, 17105-041, GIBCO, Life Technology) at 37° C. incubator under rotating conditions for 8-12 h, 0.05% trypsin/EDTA for 5 min and DNase I for 5 min. Samples were triturated through 20 G needles and cells filtered through a 100-µm cell strainer. After removing the red blood cells, cell suspension was filtered through a 40-µm cell strainer and collected in WIT media (01-0009-500, Stemgent, San Diego, Calif.). These cells were used as bulk HPCa cells. CD44+ HPCa cells were obtained by sorting TROP2+CD44+ cells from freshly prepared bulk cells (21). Antibodies used herein included mouse IgG2a APC (allophycocyanin) isotype control, APC-conjugated anti-human TROP-2 monoclonal antibody, and PE-conjugated mouse anti-human CD44 or mouse IgG2b.

Transfection and Lentiviral Infection

In general, bulk or freshly purified CD44+ PCa cells and HPCa cells were transfected with neutral control microRNA or miR-199a-3p mimics (3p) using lipofectamine RNAiMAX (Invitrogen, Life Technology). In some experiments, bulk or purified CD44$^+$ cells were infected with empty (pGIPZ-Ctrl) or miR-199a-3p expressing lentivirus (pGIPZ-199A) at MOI (multiplicity of infection) of 10-20 for 72 h. pGIPZ-199A vector (SEQ ID NO: 1) was established from the backbone of GIPZ lentiviral shRNA (GIPZ-Ctrl) (GE Dharmacon), in which pre-miR-199A1 and its frank sequences were cloned into XhoI (SEQ ID NO: 2) and MluI (SEQ ID NO: 3) sites (FIG. 1A). For therapeutic experiments, prostate cancer cells were infected with lenti-Ctrl or lenti-199A1 at MOI of 10-20 for 48 h followed by puromycin selection. Lenti-199A1 was constructed from the backbone of TRIPZ inducible lentiviral shRNA (lenti-Ctrl) (GE Dharmacon). The same sequence as in pGIPZ-199A was cloned into ClaI (SEQ ID NO: 4) and MluI (SEQ ID NO: 5) sites of TRIPZ inducible shRNA (FIG. 1A).

Tumor Regeneration and Therapeutic Experiments

Tumor transplantations were performed as previously described (9,18). For subcutaneous tumor experiments, two injections per mouse, 5-10 animals per group were done. For therapeutic experiments, DU145 cells were infected with negative control (lenti-Ctrl) and miR-199a-3p lentivirus (lenti-199A) and subcutaneously implanted into NOD/SCID female mice. When tumors became palpable, two groups of mice were randomly divided into two subgroups, each one of which was administrated with the doxycycline in the food (2 µg). Tumor volume was then measured every 2-3 days for approximately two months.

Site-Specific Mutagenesis and Luciferase Assays

The luciferase reporter (pMIR-REPORT, Ambion) carrying the wild-type (WT) human CD44 3'-UTR fragment was described previously (9). Specifically, the human CD44 3'-UTR was amplified and cloned into SacI and HindIII of pMIR-REPORT (Table 1). Mutant CD44 3'-UTR construct was performed using QuickChange II Site-Directed Mutagenesis Kit (Agilent Technologies) and primers in Table 1. Cyclin D1, EGFR and MYC 3'-UTR wild type (WT) and mutant (MUT) sequences (Table 1) were synthesized by Sangon Biotech (Shanghai, China) and inserted into Xba I site of pGL3-basic vector (Promega). For luciferase assays (9,22), 150 ng of WT or mutant plasmid was co-transfected with 5 nmol of microRNA oligos and 1 ng of Renilla luciferase plasmid (phRL-CMV) for 48 h and the relative Firefly and Renilla luciferase activities determined by Dual-Luciferase Assay Kit (Promega).

TABLE 1

Primers and inserted sequences used for luciferase-reporter plasmids

| | |
|---|---|
| CD44 3'UTR-WT | Forward Primer: AGAGCTCCACCTACACCATTATCTTG (SEQ ID NO: 6) Reverse Primer: TAAGCTTGGAAGTCTTCAGGAGACAC (SEQ ID NO: 7) |
| CD44 3'UTR-MUT | Forward Primer: CTTAACAGATGCAATGTGCctgTcATTGTTTCATTGCGAATC (SEQ ID NO: 8) Reverse Primer: GATTCGCAATGAAACAATgAcAgGCACATTGCATCTGTTAAG (SEQ ID NO: 9) |
| cyclin D1 3'UTR-WT | TAATCTGTTATGTACTAGTGTTCTGTTTGTTATTGTTTTGTT AATTACACCATAATGCTAATTTAAAGAGACTCCAAATCTCAA TGAAGCCAGCTCACAGTGCTGTGTGCCCCGGTCACCTAGCAA GCTGCCGAACCAAAAGAATTTGCACCCCGCTGCGGGCCCACG TGGTTGGGGCCCTGCCCTGGCAGGGTCATCCTGTGCTCGG (SEQ ID NO: 10) |

TABLE 1-continued

Primers and inserted sequences used for luciferase-reporter plasmids

```
cyclin   TAATCTGTTATGTACTAGTGTTCTGTTTGTTATTGTTTTGTT
D1       AATTACACCATAATGCTAATTTAAAGAGACTCCAAATCTCAA
3'UTR-   TGAAGCCAGCTCACAGTCAGCTGTGCCCCGGTCACCTAGCAA
MUT      GCTGCCGAACCAAAAGAATTTGCACCCCGCTGCGGGCCCACG
         TGGTTGGGGCCCTGCCCTGGCAGGGTCATCCTGTGCTCGG
         (SEQ ID NO: 11)

EGFR     ACCTCAGACCGATTAAACGCAAATCTCTGGGGCTGAAACCCA
3'UTR-   AGCATTCGTAGTTTTTAAAGCTCCTGAGGTCATTCCAATGTG
WT       CGGGCCAAAGTTGAGAACTACTGGCCTAGGGATTAGCCACAAG
         GACATGGACTTGGAGGCAAATTCTGCAGGTGTATGTGATTCT
         CAGGCCTAGAGAGCTAAGACACAAAGACCTCCACATCTG
         (SEQ ID NO: 12)

EGFR     ACCTCAGACCGATTAAACGCAAATCTCTGGGGCTGAAACCCA
3'UTR-   AGCATTCGTAGTTTTTAAAGCTCCTGAGGTCATTCCAATGTG
MUT      CGGGCCAAAGTTGAGAAATCCCAGCCTAGGGATTAGCCACAAG
         GACATGGACTTGGAGGCAAATTCTGCAGGTGTATGTGATTCT
         CAGGCCTAGAGAGCTAAGACACAAAGACCTCCACATCTG
         (SEQ ID NO: 13)

MYC      TGCTCCATGAGGAGACACCGCCCACCACCAGCAGCGACTCTG
3'UTR-   AGGAGGAACAAGAAGATGAGGAAGAAATCGATGTTGTTTCTG
WT       TGGAAAAGAGGCAGGCTCCTGGCAAAAGGTCAGAGTCTGGAT
         CACCTTCTGCTGGAGGCCACAGCAAACCTCCTCACAGCCCAC
         TGGTCCTCAAGAGGTGCCACGTCTCCACACATCAGCACA
         (SEQ ID NO: 14)

MYC      TGCTCCATGAGGAGACACCGCCCACCACCAGCAGCGACTCTG
3'UTR-   AGGAGGAACAAGAAGATGAGGAAGAAATCGATGTTGTTTCTG
MUT      TGGAAAAGAGGCAGGCGCTCTGCAAAAGGTCAGAGTCTGGAT
         CACCTTCTGCTGGAGGCCACAGCAAACCTCCTCACAGCCCAC
         TGGTCCTCAAGAGGTGCCACGTCTCCACACATCAGCACA
         (SEQ ID NO: 15)
```

Note:
The seed sequence and mutant region are in Bold.

Real-Time Reverse Transcription-Polymerase Chain Reaction (RT-qPCR) and Western Blotting In brief, total RNA was extracted from unsorted or purified CD44$^+$ and CD44$^-$ PCa cells by using the mirVana™ microRNA Isolation Kit (P/N: 1560, Ambion, Austin, Tex.). cDNA was synthesized using 10 ng of total RNA and RT primers for RNU48, the internal "housekeeping" microRNA control or for miR-199a-3p. qPCR was performed using the synthesized cDNA, and RNU48 or miR-199a-3p microRNA primers (Ambion, Life Technology). The raw data using the ΔCt method was first processed, by which the expression level of miR-199a-3p in each sample was normalized to that of RNU48. Then the relative expression levels of miR-199a-3p (and/or miR-199a-5p) in different experimental groups (e.g., CD44$^+$ vs. CD44$^-$ cell, NC vs. miR-199a-3p, lenti-Ctrl vs. lenti-199A1, etc) was compared by normalizing to the corresponding CD44$^-$, NC, or Ctrl group (which was considered as 1). Western Blotting was routinely performed using primary antibodies, ECL Mouse IgG, HRP-Linked whole Ab (NA931V, GE Healthcare Life Sciences), ECL Rabbit IgG, and HRP-Linked Whole Ab (NA934V, GE Healthcare Life Sciences).

Immunohistochemistry (IHC)

Briefly, formalin-fixed paraffin-embedded tissue sections (4 μm) were deparaffinized and hydrated in xylene followed by graded alcohols to water. Endogenous peroxidase activity were blocked with 3% H2O2 for 10 min. After antigen retrieval in 10 mM Citrate Buffer (pH 6.0), nonspecific binding was blocked by Background Sniper (BS966H, Biocare Medical) and slides were incubated with CD44, Ki-67, or lamin A antibodies at 1:100 dilution at 4° C. overnight. Next day, slides were thoroughly washed and visualized upon incubation with polymer-conjugated horseradish peroxidase and Sigma Tablet DAB.

Clonal, Sphere-Formation and Matrigel-Based Clonogenic Assays

For holoclone assays, cultured prostate cancer or human prostate cancer cells were plated at 500~5000 cells per well in sixwell plates and the number of colonies enumerated in 1-2 weeks upon crystal violet staining. For sphere-formation assays, prostate cancer cells were plated at 500~5000 cells per well in ultra-low attachment plates and cultured in WIT medium for 2-3 weeks followed by determining the number of colonies under a microscope. For Matrigel-based clonogenic assays, a mixture of 40 μl of medium with 500-5,000 cells and 40 μl of Matrigel solution were seeded along the edge of the wells in 24-well plates followed by counting the number of colonies in 2-3 weeks.

BrdU Incorporation Assays and Cell Cycle Analysis

For BrdU incorporation assays, cells plated on coverslips one day before were pulsed for 3-4 h with 10 μM BrdU (B5002, Sigma), fixed in 4% paraformaldehyde and incubated with mouse anti-human BrdU (B2531, Sigma) antibody at 4° C. overnight. After thorough washing, coverslips were incubated at room temperature for 1 h with secondary antibody, i.e., Alexa Flour 594-conjugated goat anti-mouse IgG (1:500). Coverslips were then counterstained with DAPI (1:1000) and mounted with 10 μl Gold Antifade Reagent (936590, Prolong). Images were acquired under microscope (Nikon, Eclipse E800). For cell cycle analysis, 48 h after transfection when cells reached approximately 60-80% confluence, cells were harvested and fixed in cold 70% ethanol and incubated in propidium iodide (PI) solution, with 20 μg/ml PI, 50 μg/ml Rnase A, 0.02% NP40 in PBS at 4° C. for 30 min and then used for DNA content analysis.

Statistical Analysis

In general, statistical differences and variances for cell number, percentage of CD44$^+$ cells, DNA content, sphere/cloning efficiency and tumor weights, etc. were determined by Student's t-test. The Fisher's exact and χ2 tests were used to compare tumor incidence. All results were presented as mean±S.D or mean±SEM. P<0.05 was considered statistically significant.

Example 2 miR-199a-3p Inhibits PCa Cell Proliferation In Vitro miR-199a-3p, encoded from chromosome 19p13.2 (SEQ ID NO: 18) or chromosome 1q24.3 (SEQ ID NO: 19) (FIG. 1B), has been reported as a tumor suppressive microRNA in several tumor types. Most miR-199a-3p related studies are in hepatocellular carcinoma (HCC), in which it is reported to induce apoptosis or to suppress cell proliferation by delaying G1/S transition (23-25). Overexpression of miR-199a-3p has also been reported to result in caspase-dependent and -independent apoptosis in lung cancer (26) and G1 phase cell-cycle arrest in osteosarcoma cells (27). The previous study suggested that miR-199a-3p is underexpresssed in several prostate cancer stem/progenitor cell populations, especially in CD44+ prostate cancer cells (9,15).

Figure 1C:
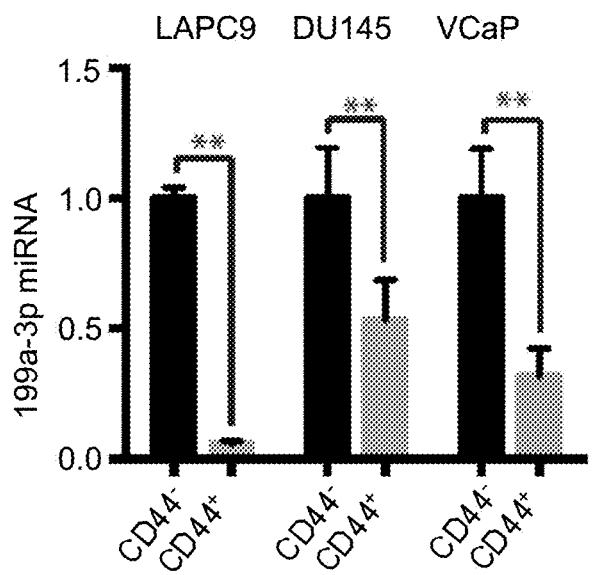
Figure 1D:
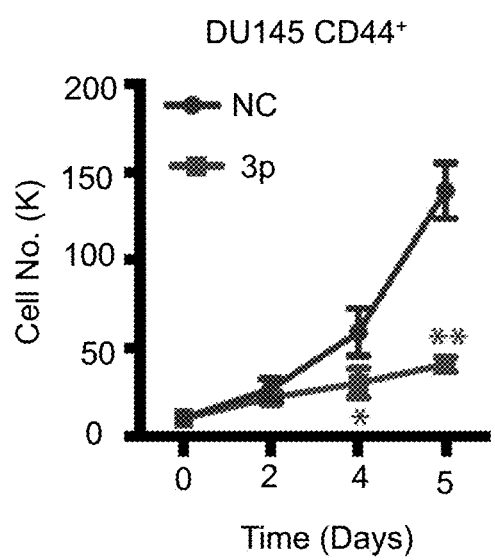
Figure 1E:
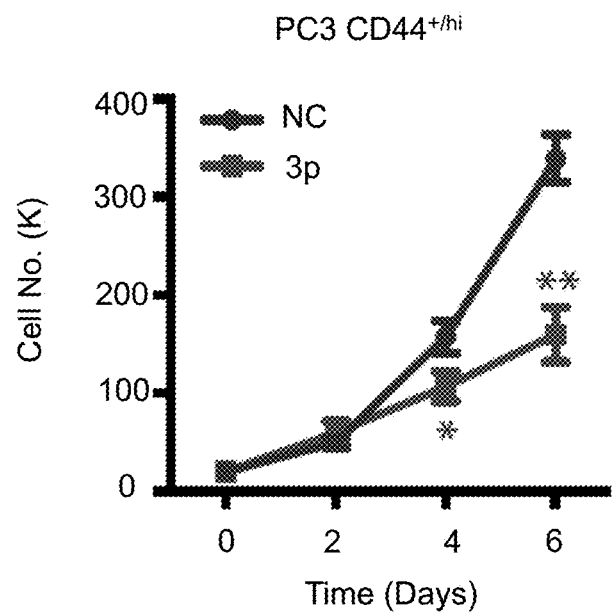
Figure 1F:
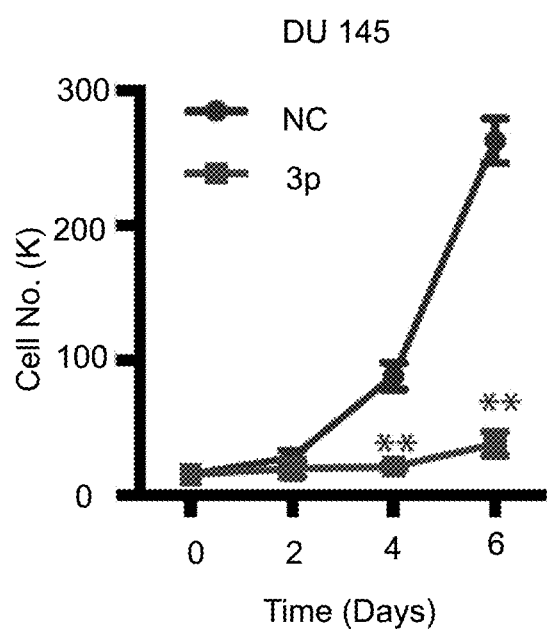
Figure 1G:
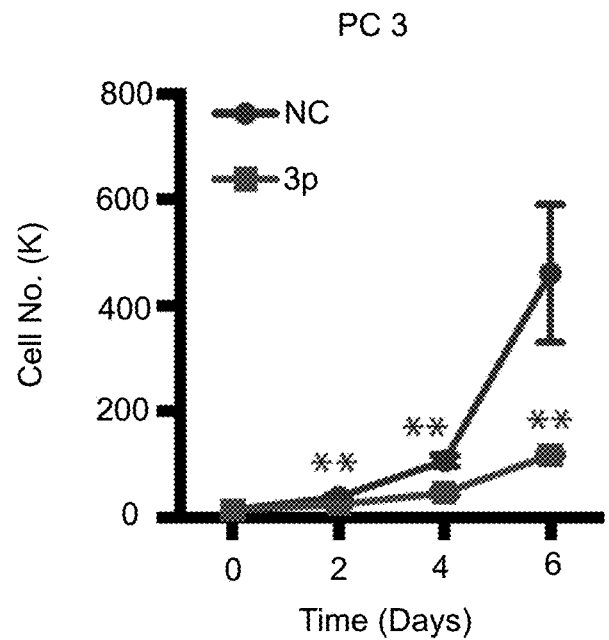
Figure 1H:
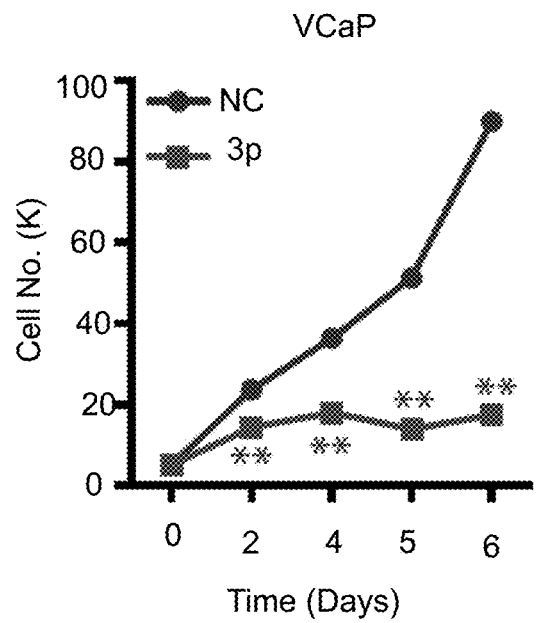
Figure 1I:
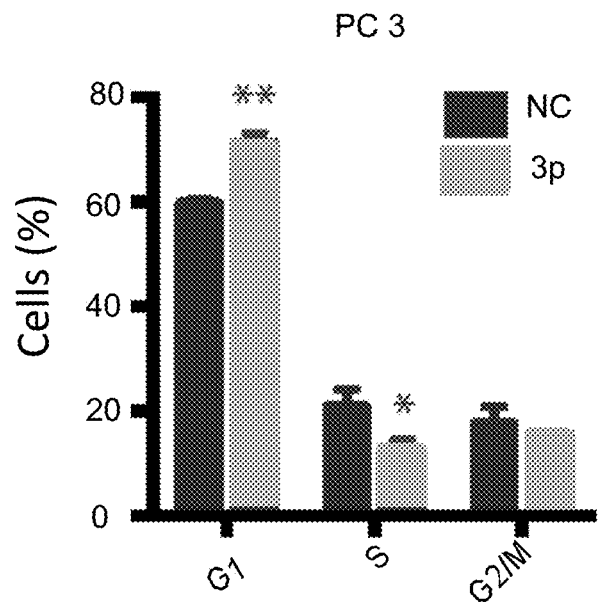
Figure 1J:
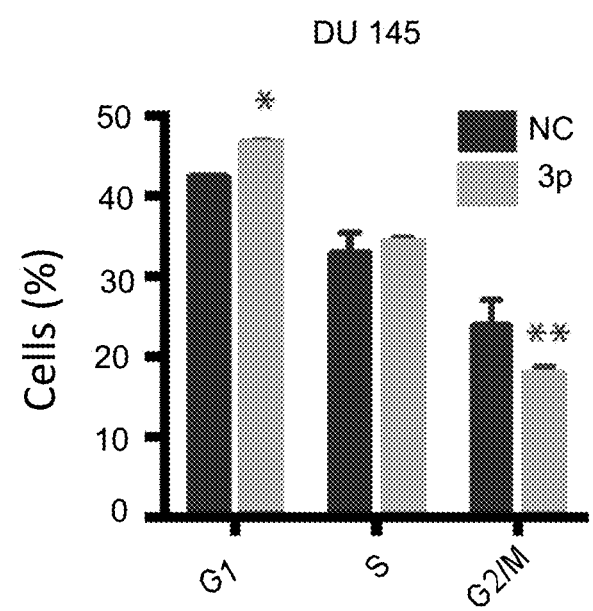
Figure 1K:
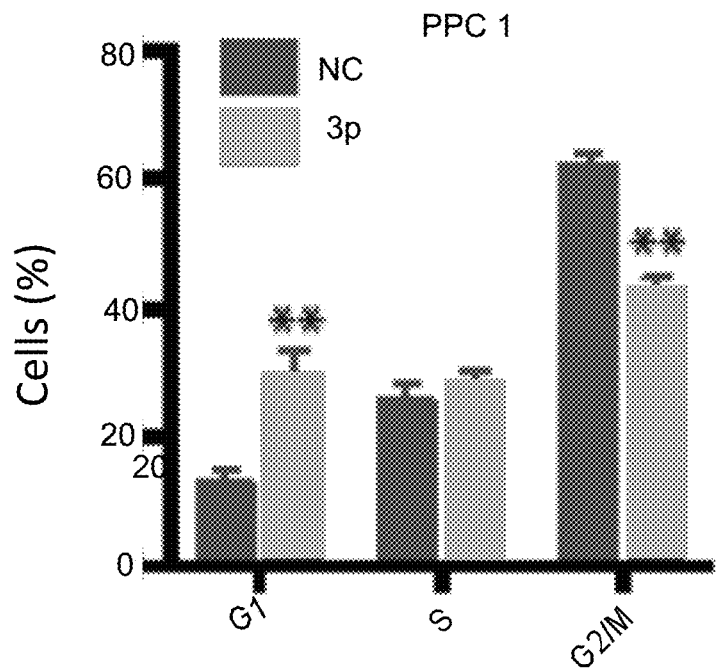
Figure 1L:
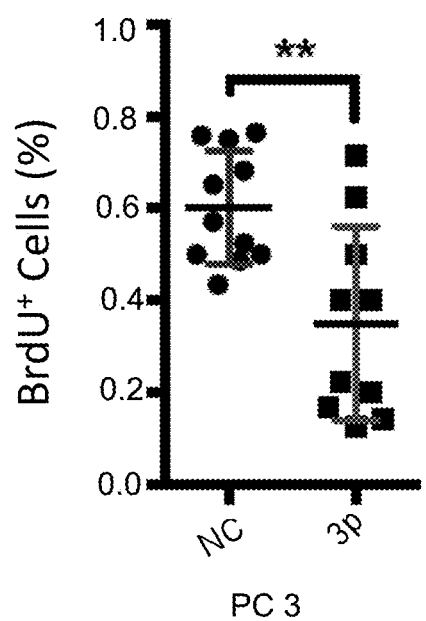
Figure 1M:
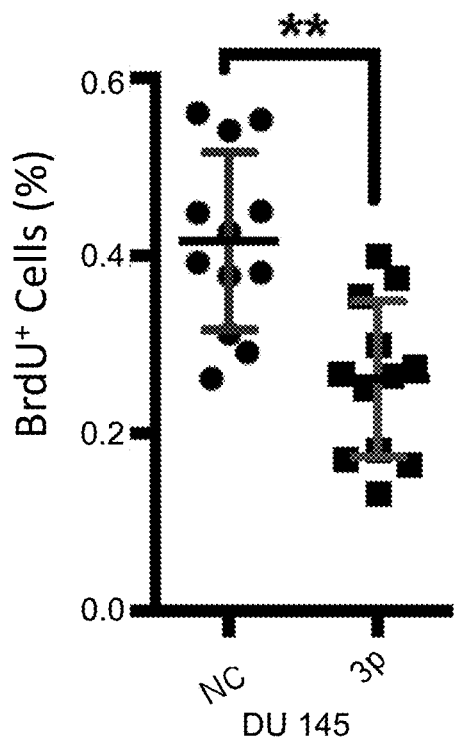

In the present invention, miR-199a-3p expression in the CD44+ cell population, freshly purified from DU145 cultures and two xenografts, i.e., LAPC9 and VcaP, was re-evaluated. The results revealed significant under-expression of miR-199a-3p in all three CD44+ prostate cancer cell populations (FIG. 1C). In the forgoing sections, the biological functions of miR-199a-3p in two AR+/PSA+ (i.e., LAPC9 and VCaP) and three AR-/PSAPCa cell line (DU145, PC3, and PPC-1) and xenograft (LAPC9 and VCaP) models were determined. In these 5 prostate cancer models, 3 (i.e., LAPC9, VCaP, and Du145) have well-demarcated CD44$^+$ and CD44$^-$ subpopulations whereas PC3 and PPC-1 cells are nearly 100% positive although CD44$^{+/hi}$ and CD44$^{-/lo}$ subpopulations could still be fractionated out (6,9,10).

miR-199a-3p mimics or negative control (NC) oligos were transfected into either purified CD44$^+$ (FIG. 1D-E) or bulk (FIGS. 1F-1H) prostate cancer cells. The transfection efficiency was validated by qPCR analysis. miR-199a-3p reduced the live cell numbers in both purified CD44+ (FIGS. 1D-1E) and bulk (FIGS. 1F-1H) prostate cancer cells. To uncover the potential mechanisms underlying the prostate cancer cell "growth-inhibitory" effects of miR-199a-3p, cell proliferation was assessed by BrdU incorporation and cell-cycle (i.e., DNA content) analysis, cell death by Annexin V and PI staining, and cell senescence by senescence-associated β-galactosidase staining. It was observed that miR-199a-3p treatment increased the % of G1-phase cells in PC3 (FIG. 1I), DU145 (FIG. 1J), and PPC-1 (FIG. 1K) cultures. For example, in PC3 cells, the G1-phase cells increased from ~59% in the negative control group to ~71% in the miR-199a-3p group (FIG. 1I). Interestingly, accompanying the increase in G1-phase cells, miR-199a-3p reduced S-phase cells in PC3 (FIG. 1I) but reduced G2/Mphase cells in DU145 (FIG. 1J) and PPC-1 (FIG. 1K) cells. These results suggest that in 3 prostate cancer cell types, miR-199a-3p overexpression causes G1 cell-cycle arrest with concomitant decrease in S or G2/M phase cells. Consistent with the cell-cycle analysis, miR-199a-3p inhibited BrdU incorporation in DU145 (FIG. 1L) and PC3 (FIG. 1M) cells. In contrast, no significant difference was observed between negative control and miR-199a-3p treated prostate cancer cells in early apoptotic, late apoptotic or late necrotic cells. Neither miR-199a-3p nor negative control induced appreciable cell senescence in the 3 prostate cancer cell types. Taken together, these observations indicate that enforced expression of miR-199a-3p inhibits prostate cancer cell cell-cycle progression and proliferation without affecting cell death or senescence.

Example 3 miR-199a-3p Inhibits Prostate Cancer Stem Cell Properties

Figure 2A:
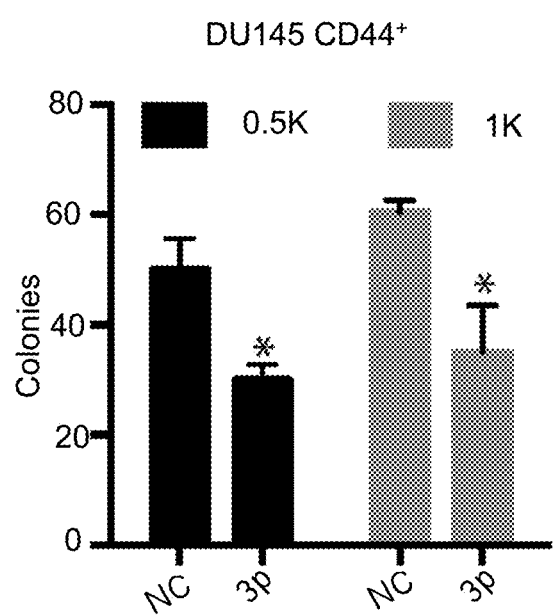
FIGS. 2A-2G illustrate that miR-199a-3p suppresses clonogenic and sphere-forming properties in prostate cancer cells.
Figure 2B:
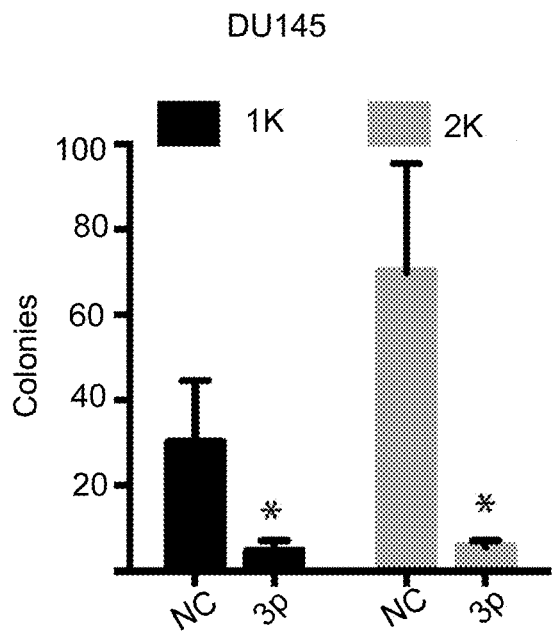
Figure 2C:
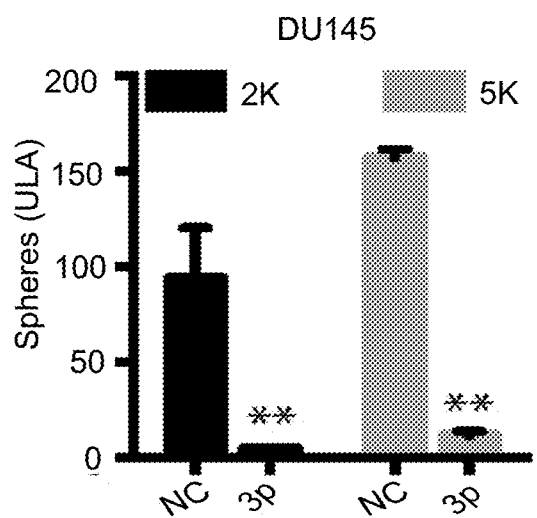
Figure 2D:
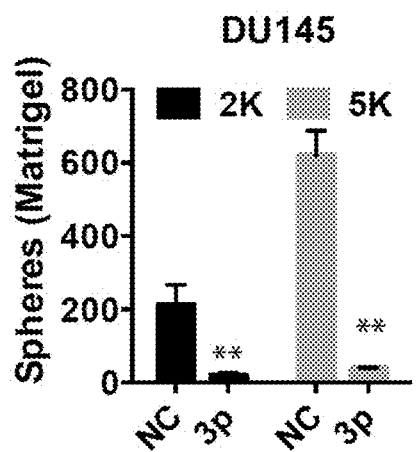
Figure 2E:
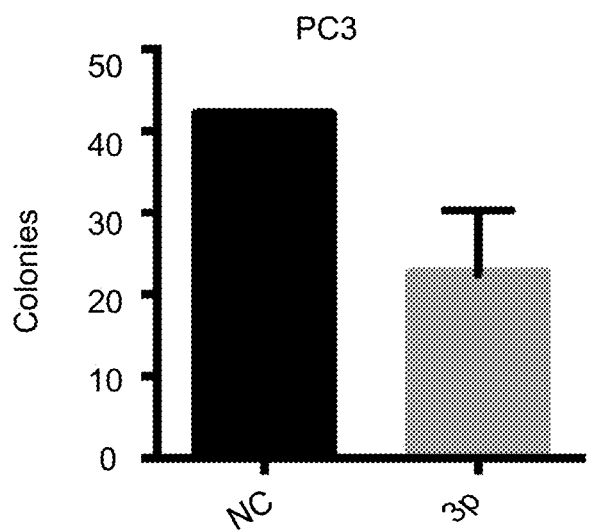
Figure 2F:
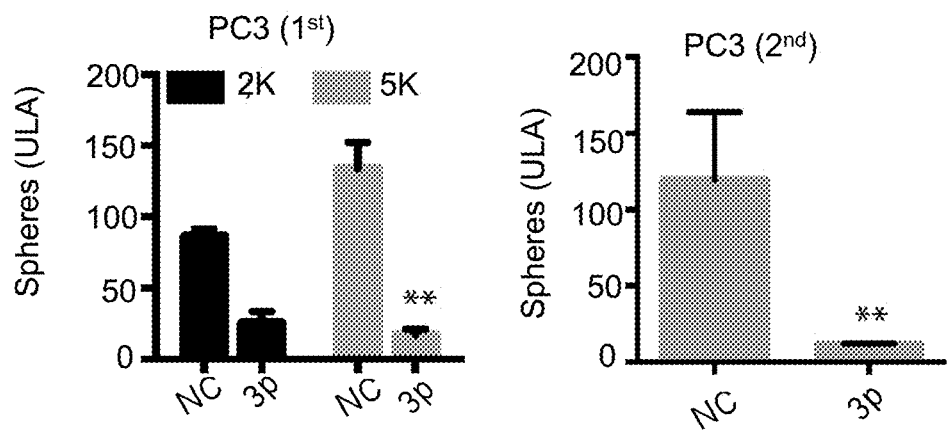
Figure 2G:
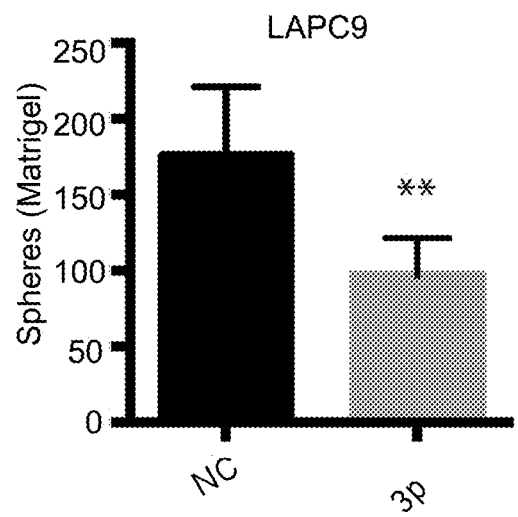

It was reported that miR-199a-3p was downregulated under hypoxia and decreased the clonal capacity in ovarian cancer cells (28). Prostate cancer cell holoclones contain self-renewing tumor-initiating cells (20) and spheres formed under anchorage-independent conditions harbor tumor-initiating cells (6,9,18). To test the effects of miR-199a-3p on prostate cancer stem cell properties, holoclone, Matrigel-based clonogenic, and ultra-low attachment (ULA) based sphere-formation assays (FIG. 2), was employed which have been widely used to measure the activity of stem/progenitor cells. Purified CD44+ DU145 cells transfected with miR-199a-3p oligos exhibited significantly reduced cloning efficiency compared with the cells transected with negative control oligos (FIG. 2A). Bulk DU145 cells were also dramatically suppressed by miR-199a-3p in all of the above-mentioned three assays (FIGS. 2B-2D). miR-199a-3p showed similar inhibitory effects in PC3 and LACP9 cells (FIGS. 2E-2G). Notably, miR-199a-3p inhibited secondary sphere formation in PC3 cells (FIG. 2F), suggesting that miR-199a-3p may inhibit prostate cancer stem cell self-renewal in vitro. Collectively, these observations demonstrate that miR-199a-3p negatively regulate prostate cancer stem cell properties.

Figure 3A:
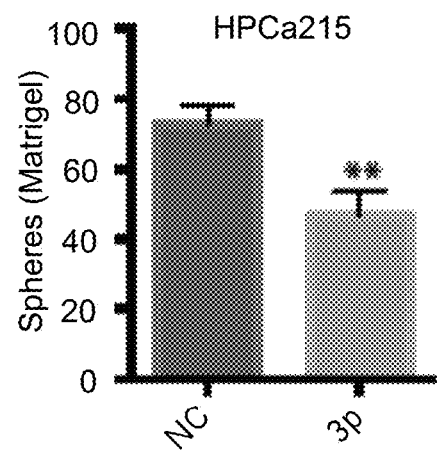
FIGS. 3A-3F illustrate that miR-199a-3p inhibits clonal and clonogenic properties of human prostate cancer cells (HPCa).
Figure 3B:
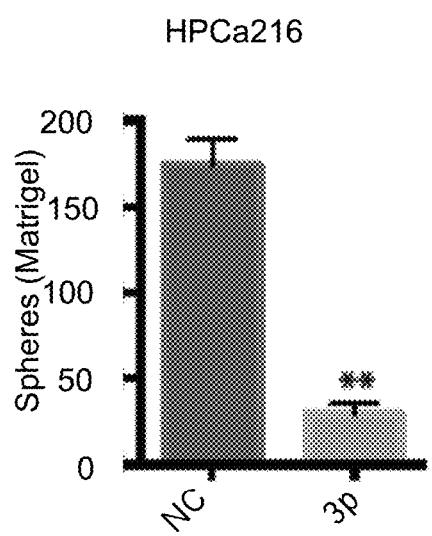
Figure 3C:
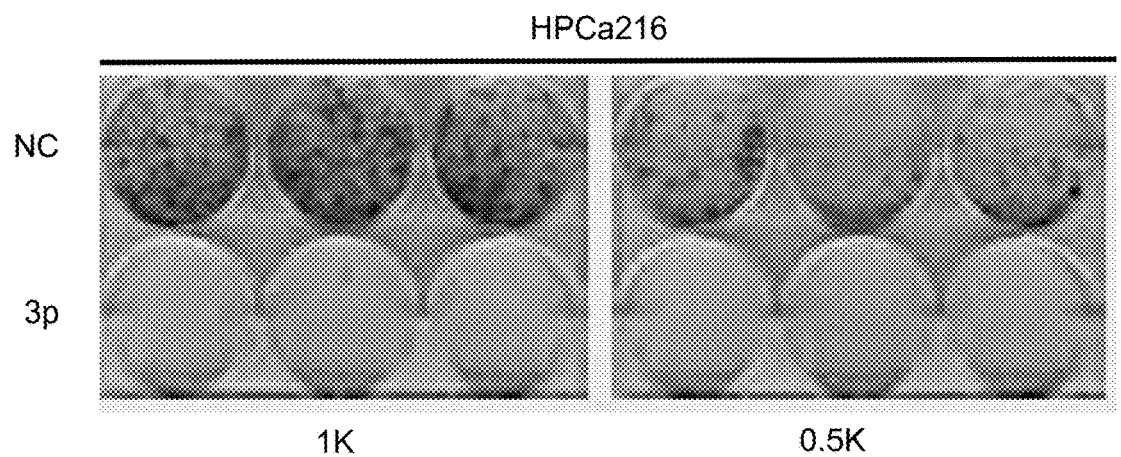
Figure 3D:
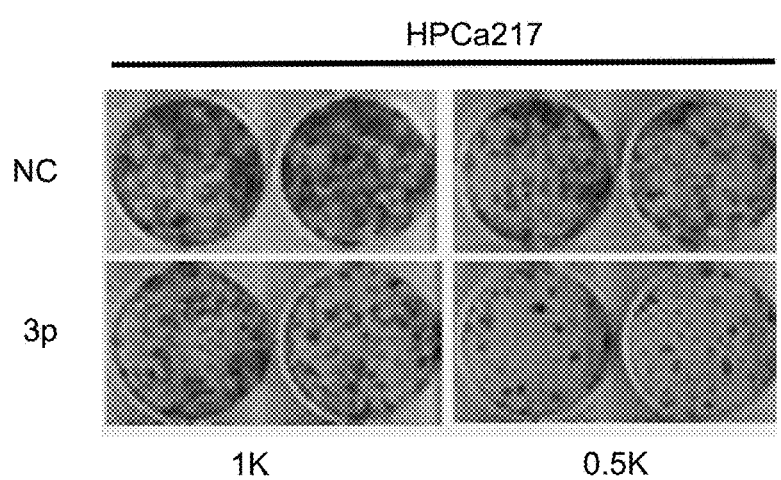
Figure 3E:
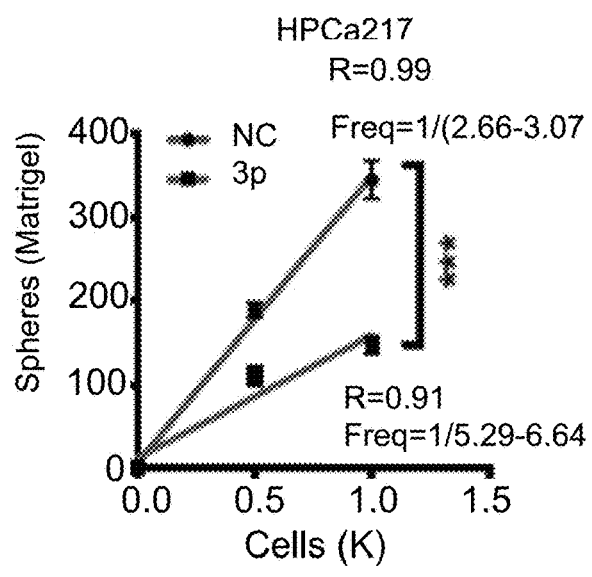
Figure 3F:
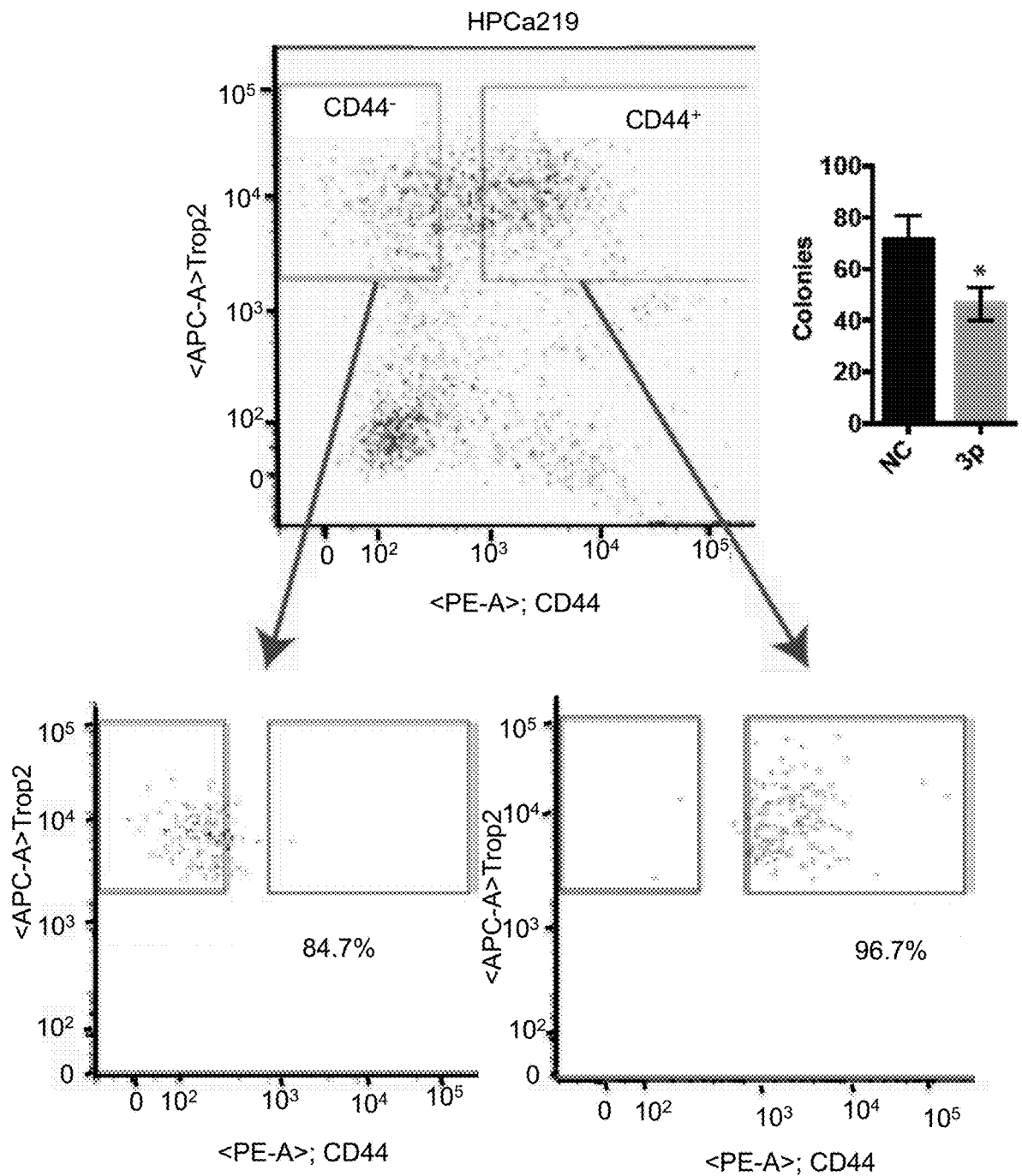

Example 4 miR-199a-3p Demonstrates Inhibitory Effects in Primary Human Prostate Cancer (HPCa) Cells The miR-199a-3p expression level is generally decreased in cancers in comparison to their normal counterparts (23, 25,27,29). In prostate cancer, miR-199a-3p expression is found to be negatively associated with tumor staging and differentiation (17). However, very few functional studies have been performed in human primary cancer samples. Consequently, the biological functions of miR-199a-3p in 4 human prostate cancer specimens with ~100% tumor involvement were studied. Tumor pieces were quickly processed and epithelial human prostate cancer cells were purified out (see Methods) and transfected with miR-199a-3p or negative control oligos. Bulk human prostate cancer cells with miR-199a-3p overexpression demonstrated much lower sphere-forming (FIGS. 3A-3B) and clonal (FIGS. 3C-3D) capacities than the corresponding human prostate cancer cells transfected with negative control oligos. A limiting dilution sphere formation assay in HPCa217 cells was also performed and the results demonstrated that miR-199a significantly reduced the sphere-forming activities (FIG. 3E). Finally, the CD44+/CD44− HPCa219 epithelial cells were purified out (i.e., using the TROP2 as the epithelial marker (30) (FIG. 3F, left; purities for each population shown below) and clonal analysis was performed. miR-199a-3p overexpression significantly reduced colony formation of the CD44+ HPCa219 cells (FIG. 3F, right). As observed before that the CD44− HPCa cells generally manifest low/no clonal capacity (10), the CD44− HPCa219 cells hardly formed any holoclones (data not shown). These results indicate that miR-199a-3p also manifests inhibitory effects in primary prostate cancer cells.

Figures 4A, 4B, 4C:
FIGS. 4A-4G illustrate miR-199a-3p inhibits xenograft tumor regeneration.
Figure 4D:
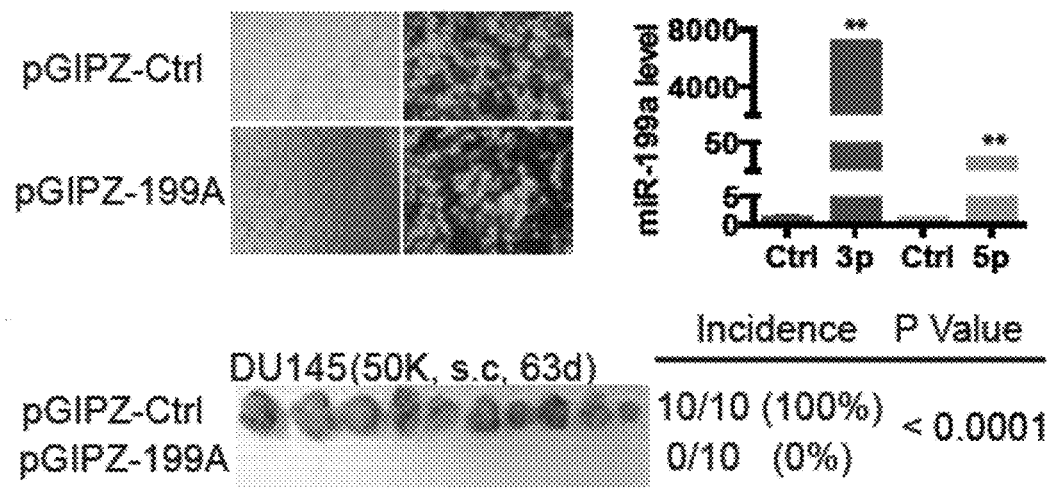
Figure 4E:
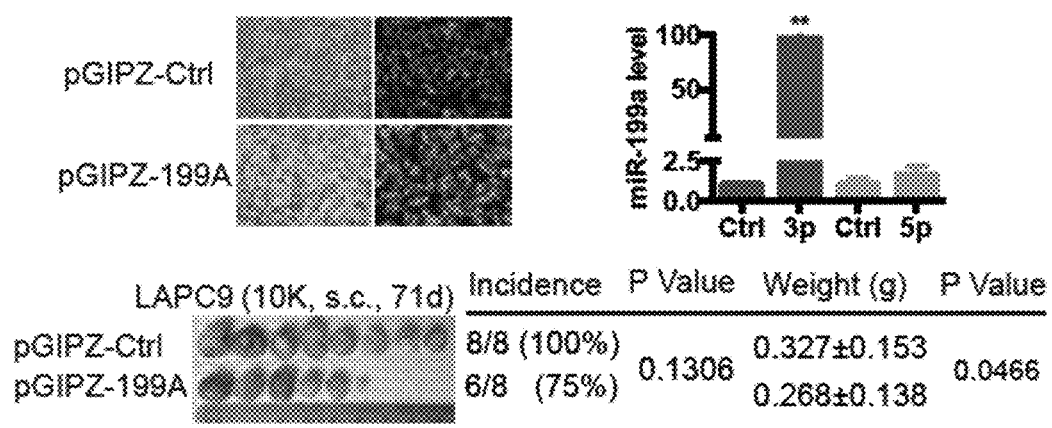

Example 5 miR-199a-3p Suppresses Prostate Tumor Regeneration In Vivo miR-199a-3p has been shown to inhibit peritoneal dissemination of ovarian carcinoma cells in a xenograft model (28). However, studies on in vivo functions of miR-199a-3p in human cancers are generally very limited. To determine whether miR-199a-3p possesses tumor-inhibitory effects in prostate cancer, limiting-dilution assays (LDAs) in immunocompromised mice by were carried out monitoring tumor latency, incidence and endpoint weight. First of all, miR-199a-3p and negative control oligos were transfected into freshly purified CD44+ DU145 cells and subcutaneously implanted into NOD/SCID mice. As shown in FIG. 4A, at 100,000 cell injections, miR-199a-3p significantly inhibited tumor growth as manifested by reduced tumor sizes. At 10,000 injections, miR-199a-3p inhibited both tumor incidence and tumor growth (FIG. 4A; note that miR-199a-3p overexpressing CD44+DU145 cells regenerated tumors that were only ¹⁄₁₀ of the tumors derived from negative control-transfected CD44+DU145 cells). Impressively, in two independent experiments, miR-199a-3p nearly completely abolished tumor regeneration from bulk DU145 cells (FIG. 4B). miR-199a-3p overexpression by oligo transfection also inhibited tumor regeneration in PPC-1 and PC3 cells. To further investigate the tumor-inhibitory effects of miR-199a-3p, a lentiviral expression vector that encodes human miR- 199A1 (FIG. 4C) was constructed. Consistent with earlier observations, transduction of DU145 cells with miR-199A1 did not cause appreciable cell death but led to significantly increased amount of miR-199a-3p (FIG. 4D). Strikingly, miR-199a-3p overexpression completely inhibited tumor regeneration from bulk DU145 cell (FIG. 4D). Bulk LAPC9 cells purified from androgen-dependent xenografts were then infected with the control or miR-199A1 encoding lentivirus for ~48 h. Again no significant cell death in LAPC9 cells infected with either virus was observed (FIG. 4E, left). pGIPZ-199A infection of LAPC9 cells for a short period of time (i.e., 48 h) led to only ~100 fold increase in miR-199a-3p levels (FIG. 4E, a, right), much lower than in puromycin-selected DU145 cells (FIG. 4D, right). Nevertheless, miR-199a-3p overexpression still reduced tumor incidence and weight in LAPC9 cells (FIG. 4E).

Note that the miR-199A1 lentivector did encode miR-199a-5p; however, the miR-199a-5p levels in both DU145 and LAPC9 cells were much lower than miR-199a-3p levels (FIGS. 4D-4E), suggesting that the PCa-suppressive effects observed were largely ascribed to miR-199a-3p.

Figure 4F:
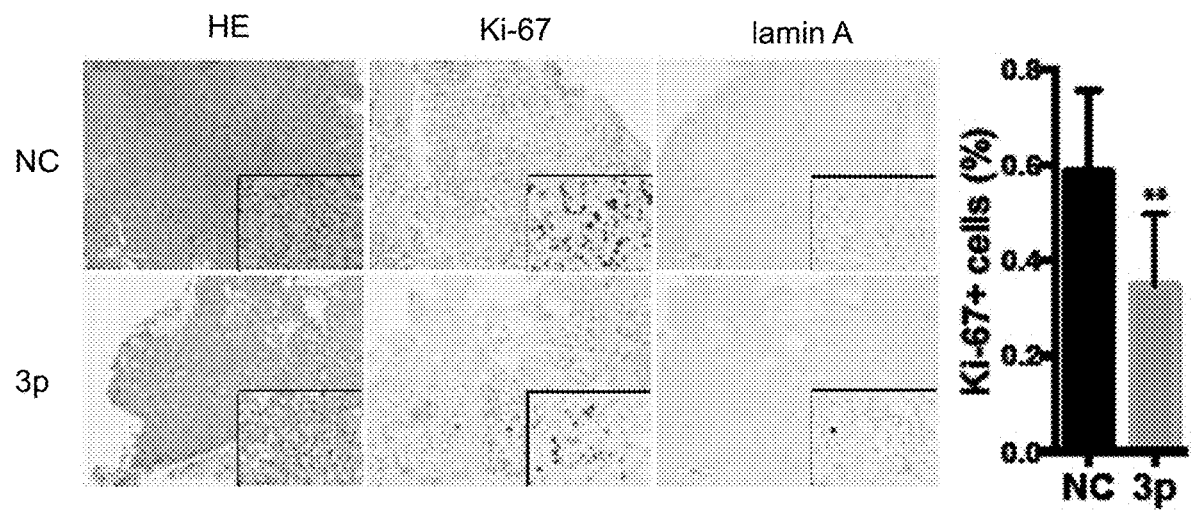
Figure 4G:
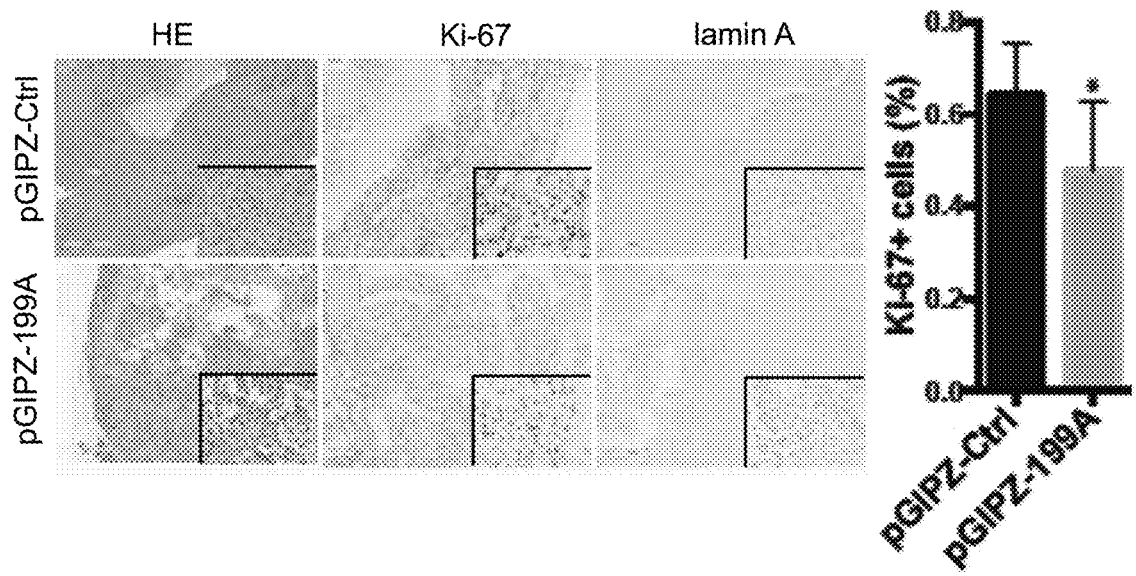

HE and IHC analysis of proliferation (by Ki-67 staining) and apoptosis (by cleaved lamin A staining) in endpoint DU145 (FIG. 4F) and LAPC9 (FIG. 4G) tumors was performed. In both cases, it was observed, in miR-199a-3p overexpressing tumors, reduced cellularity (FIGS. 4F-4G; compare panels a vs b) and Ki-67+ cells (FIGS. 4F-4G; compare panels c vs d). In contrast, both DU145 and LAPC9 tumors showed very little apoptotic (i.e., lamin A+) cells and there were no differences between control and miR-199a-3p tumors (FIGS. 4F-4G). Taken together, the above experiments indicate that miR-199a-3p inhibits prostate tumor regeneration and growth by inhibiting cell proliferation without causing cell death.

Example 6 miR-199a-3p Exhibits Therapeutic Potential in a PCa Xenograft Models

Figure 5A:
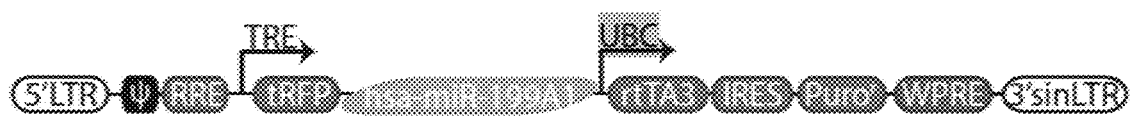
FIGS. 5A-5D illustrate miR-199a-3p exhibits therapeutic potential in PCa cells.
Figure 5B:
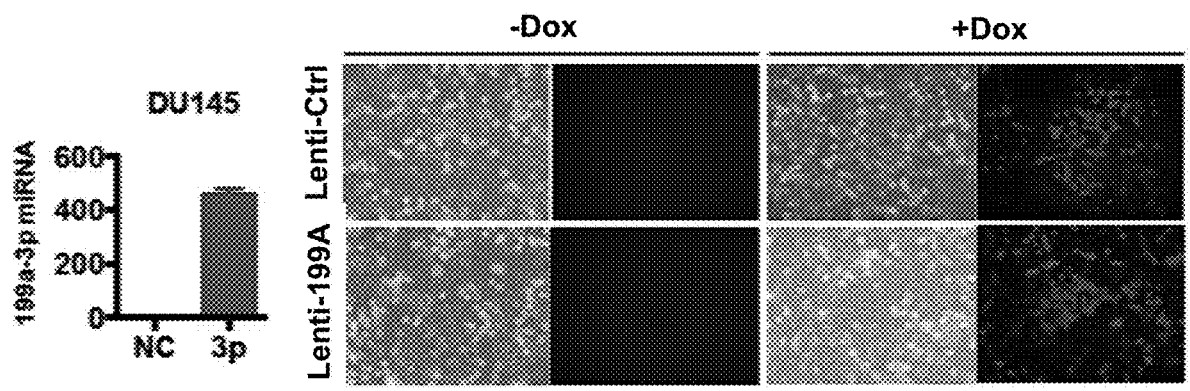
Figure 5C:
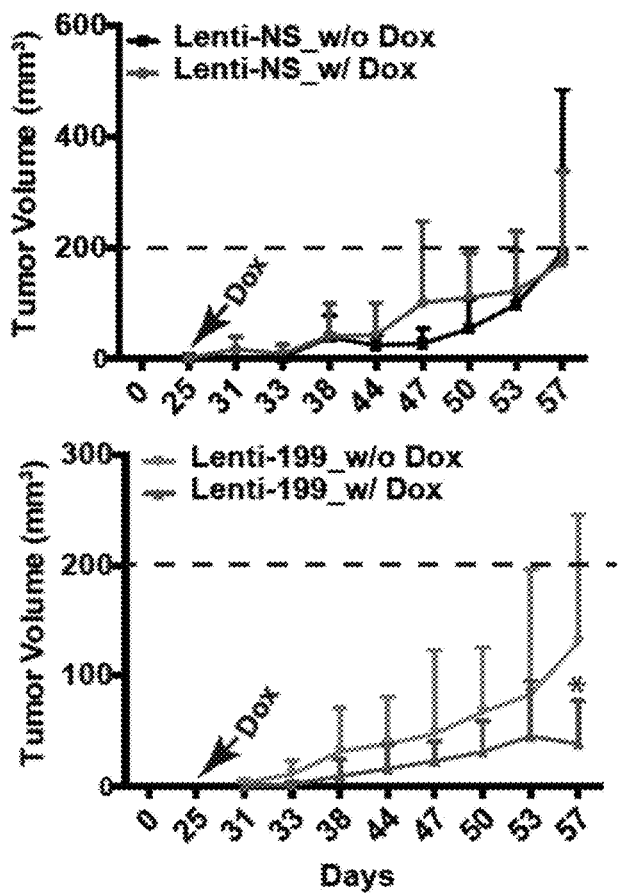
Figure 5D:
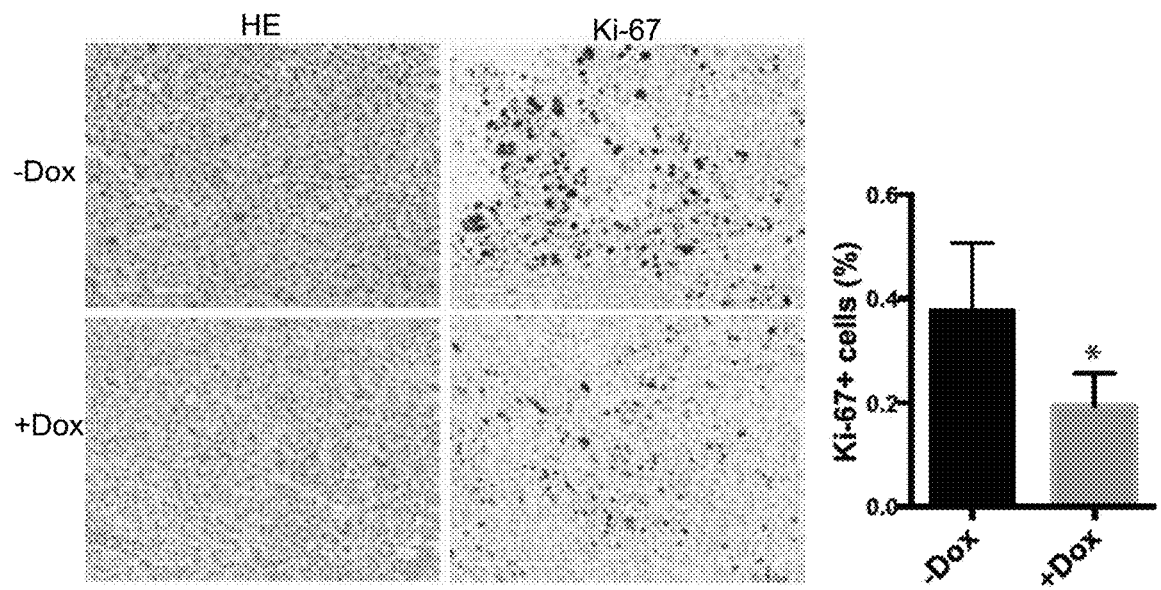

Hou et al reported the tumor-inhibitory effects of miR-199a-3p in an hepatocellular carcinoma-bearing mouse model (23). To explore the therapeutic potential of miR-199a-3p in prostate cancer, its tumor-inhibitory effects in a pre-established prostate cancer xenograft model were tested. To that end, doxycycline (Dox) inducible lentiviral system was constructed to overexpress miR-199a-3p (lenti-199a), in which primary miR-199A1 sequence was cloned downstream from the red fluorescent protein reporter (FIG. 5A). Doxycycline addition induced red fluorescent protein reporter expression and increased miR-199a-3p levels (FIG. 5B). To perform the therapeutic experiment, DU145 cells were infected with lenti-199a or empty lenti-Ctrl vector at an multiplicity of infection of 10 and implanted tumor cells subcutaneously in NOD/SCID mice. By 25 days, both lenti-Ctrl and lenti-199a groups were divided into two subgroups, one of which started to receive doxycycline-supplemented feed. As presented in FIG. 5C, bottom), doxycycline induction in the lenti-199a group slowed down tumor growth (the lenti-199a group of tumors in the absence of doxycycline, without leakage of miR-199a-3p expression), also showed slightly slower growth compared to the corresponding lenti-Ctrl group). In contrast, the lenti-Ctrl group of tumors showed similar growth kinetics in the presence or absence of doxycycline (FIG. 5C, top). IHC analysis again revealed reduced Ki-67+ cells in doxycycline-treated lenti-199a tumors (FIG. 5D) without significant differences in apoptosis. These results, collectively, reveal a therapeutic potential of miR-199a-3p in prostate cancer.

Example 7

Figure 6A:
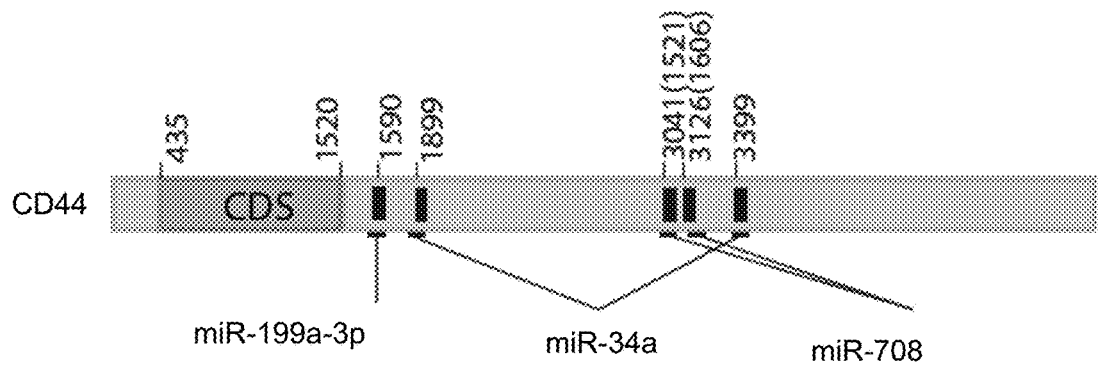
FIGS. 6A-6H illustrate CD44 is a direct target of miR-199a-3p.
Figure 6B:
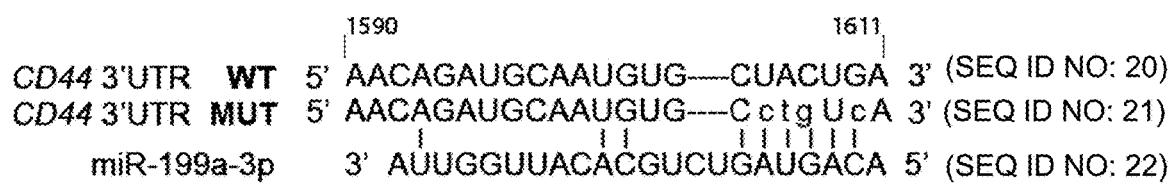
Figure 6C:
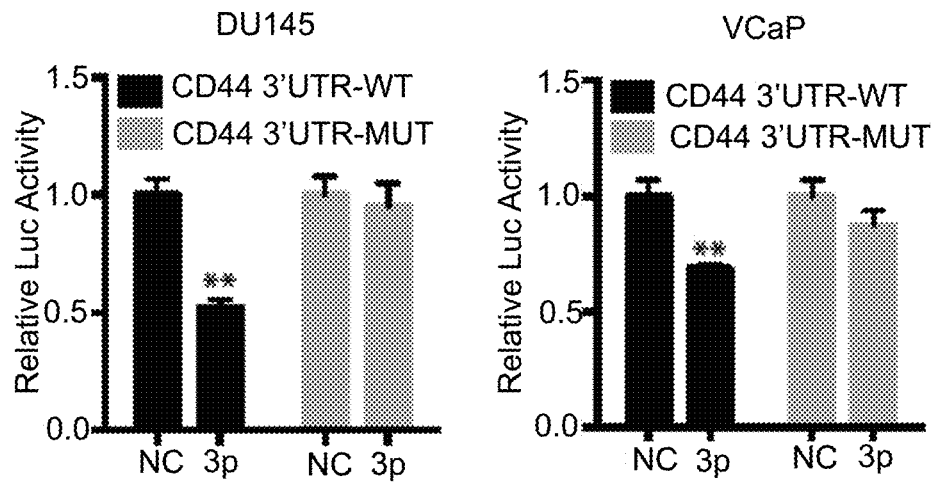
Figure 6D:
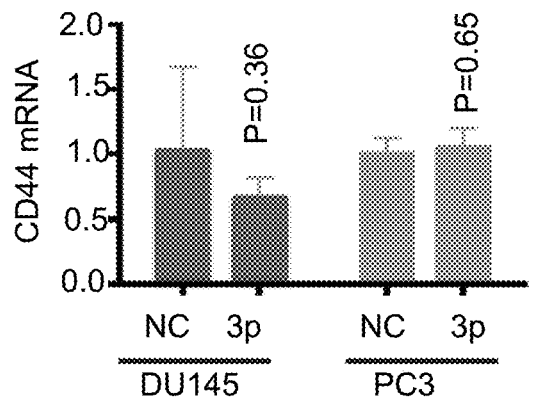
Figure 6E:
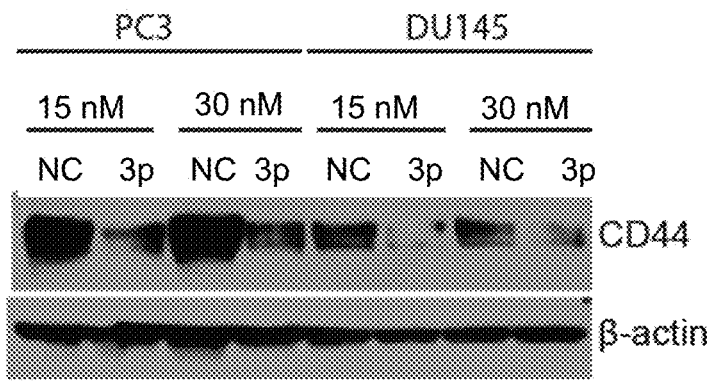
Figure 6F:
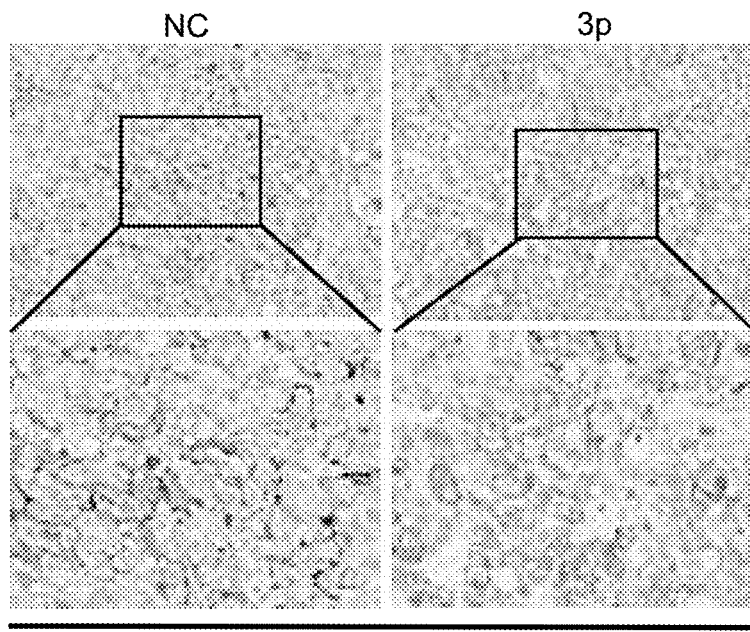
Figure 6G:
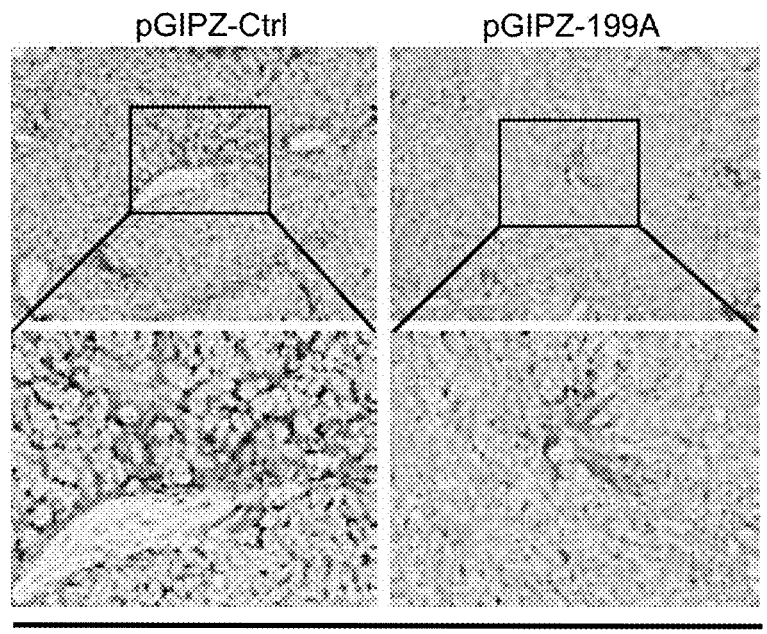
Figure 6H:
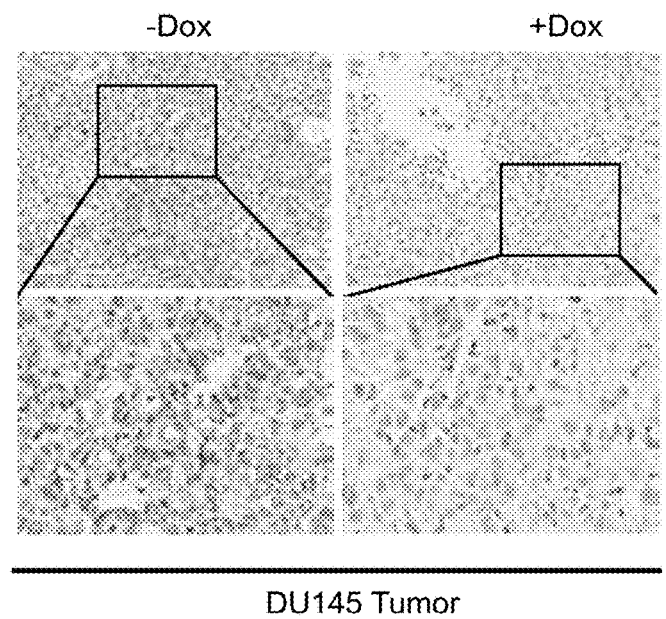

CD44 is a Direct Target of miR-199a-3p in Prostate Cancer Cells miR-199a-3p was initially uncovered from microRNA library screening for microRNAs differentially expressed in tumorigenic prostate cancer cell subpopulations (9,15). Of interest, miR-34a was found to be underexpressed in CD44+ prostate cancer cells and to inhibit prostate cancer stem cells and prostate cancer metastasis by directly targeting CD44 via binding to 2 sites at the CD44 3'-UTR (9) (FIG. 6A). Furthermore, another microRNA, miR-708, was also reported to negatively regulate PCSC activity by targeting CD44 at two different sites (31)(FIG. 6A). Finally, miR-199a-3p was reported to target CD44 in hepatocellular carcinoma cells (24). These discussions, together with the fact that miR-199a-3p was significantly underexpressed in CD44+ prostate cancer cells (15) (FIG. 6A), raise the possibility that miR-199a-3p exerts its prostate cancer-inhibitory effects via targeting, at least partly, CD44. To test this possibility, 8 different target-prediction programs were employed, 3 of which (i.e., RNA22, TargetMiner, and TargetScan) simultaneously identified a putative binding site of miR-199a-3p (SEQ ID NO: 22) at the CD44 3'-UTR (FIG. 6A-B). Site-specific mutagenesis was performed by mutating several nucleotides at the miR-199a-3p binding site on CD44 3'-UTR (FIG. 6B). Luciferase reporter assays in DU145 and VCaP cells showed that miR-199a-3p oligos co-transfected with the WT CD44 3'-UTR (SEQ ID NO:20) reduced luciferase activities (FIG. 6C). In contrast, mutations in the miR-199a-3p binding site at CD44 3'-UTR (SEQ ID NO: 21) abolished the luciferase-inhibitory effects of miR-199a-3p in both cell types (FIG. 6C). Interestingly, miR-199a-3p overexpression did not reduce CD44 mRNA levels in prostate cancer cells (FIG. 6D), suggesting that miR-199a-3p likely targets CD44 in prostate cancer cells by causing translational inhibition. Indeed, exogenously introduced miR-199a-3p reduced the CD44 protein levels in both PC3 and DU145 prostate cancer cells (FIG. 6E). Importantly, CD44 protein levels were also reduced in the endpoint tumors derived from CD44+DU145 cells transfected with miR-199a-3p oligos (FIG. 6F), LAPC9 cells infected with the pGIPZ-199A (FIG. 6G), and DU145 cells infected with the Dox-inducible lenti-199A (FIG. 6H).

Example 8

Evidence that miR-199a-3p Also Targets c-Myc, Cyclin D1, and EGFR in PCa Cells

It is well-established that a single microRNA may target multiple mRNA molecules. In fact, miR-199a-3p has been shown to suppress, in addition to CD44 (24), several other molecules including MET, mTOR, and PAK4 (23,25). It was wondered what other molecules miR-199a-3p might also target in PCa cells, either directly or indirectly. Since preceding experiments have shown that miR-199a-3p suppressed prostate cancer primarily by inhibiting cell-cycle progression and cell proliferation, efforts on 3 mitogenic molecules important for regulating prostate cancer cell proliferation, i.e., c-Myc, cyclin D1, and EGFR were subsequently focused. The c-Myc gene is known to be amplified and overexpressed in a variety of human tumors including prostate cancer (32,33) and the c-MYC protein is sufficient to immortalize benign prostatic epithelial cells (34). c-Myc has also been shown to regulate prostate cancer stem cells (35). Cyclin D1 overexpression, combined with inactivated PTEN and SMAD4 and increased SPP1, was reported to be highly predictive for poor clinical outcome in prostate cancer (36). The proliferation-promoting role of cyclin D1 in prostate cancer was also corroborated in a transgenic mouse study (37). Finally, EGFR, as an important member of the oncogenic tyrosine kinases, has been implicated in aggressive prostate cancer (38).

Figure 7A:
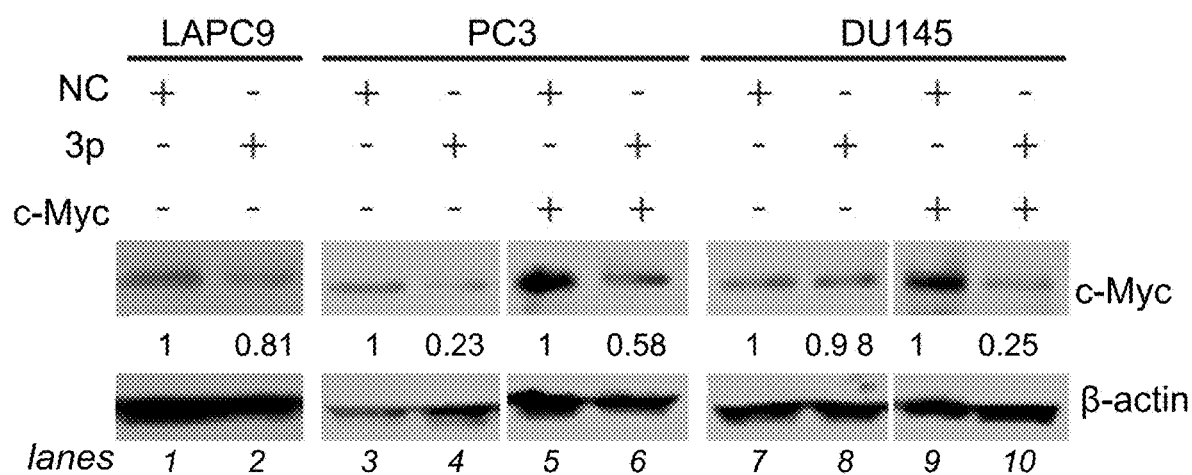
FIGS. 7A-7I illustrate miR-199a-3p also targets c-Myc and several other mitogenic signaling molecules.
Figure 7B:
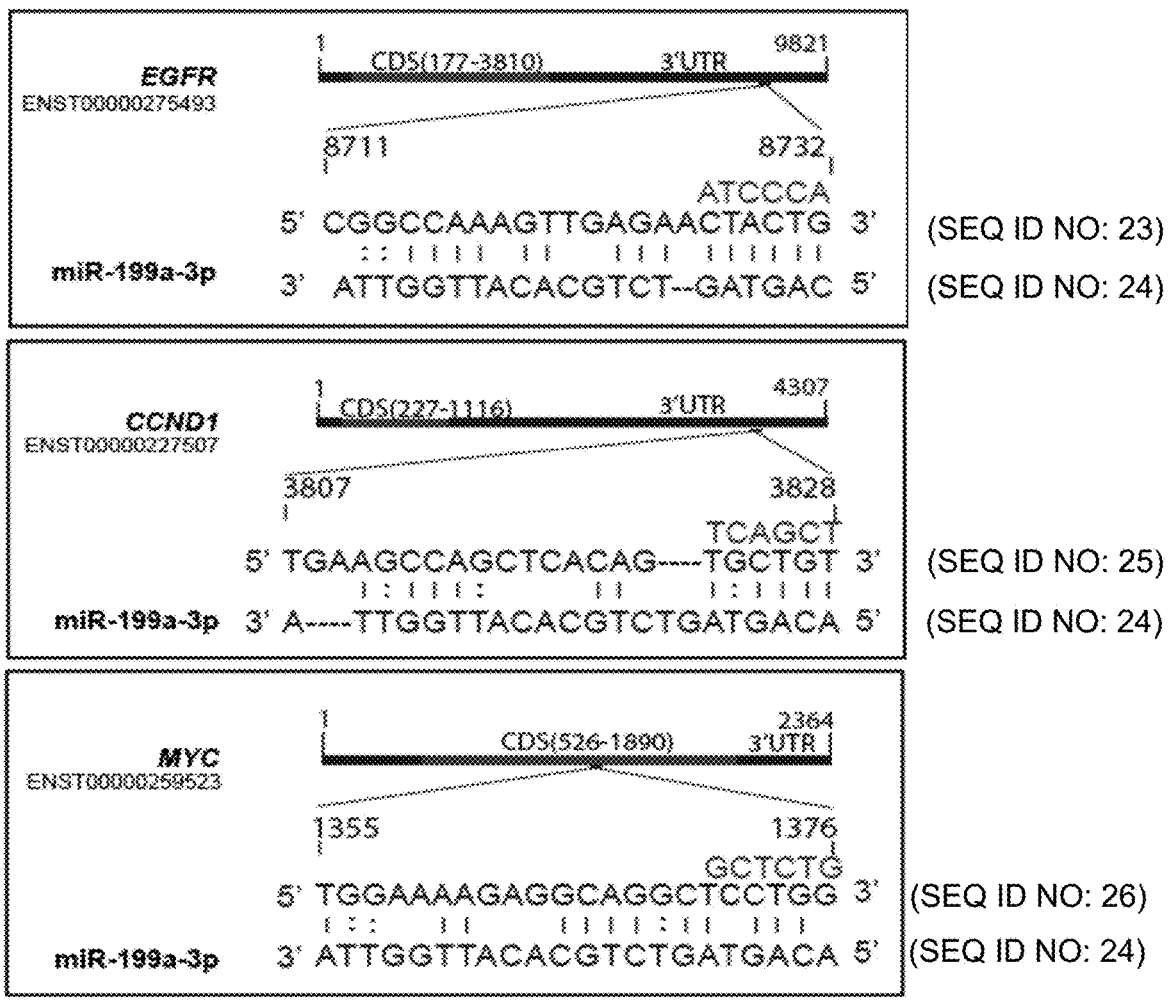

Transfecting miR-199a-3p oligos into LAPC9 and PC3 cells, decreased endogenous c-Myc protein levels (FIG. 7A; lanes 2 and 4 vs. lanes 1 and 3, respectively). Interestingly, exogenous miR-199a-3p did not significantly suppress the endogenous c-Myc protein levels in Du145 cells (FIG. 7A), suggesting that c-Myc may not be the primary mediator of the miR-199a-3p effects in Du145 cells. Of note, miR-199a-3p downregulated exogenous c-Myc protein derived from a c-Mycencoding cDNA construct in both PC3 and Du145 cells (FIG. 7A; lanes 6 and 10 vs. lanes 5 and 9, respectively), suggesting that miR-199a-3p might target c-Myc coding sequence. Indeed, a potential miR-199a-3p (SEQ ID NO: 24) binding site in the c-Myc (SEQ ID NO: 26) CDS was identified (FIG. 7B).

Figure 7C:
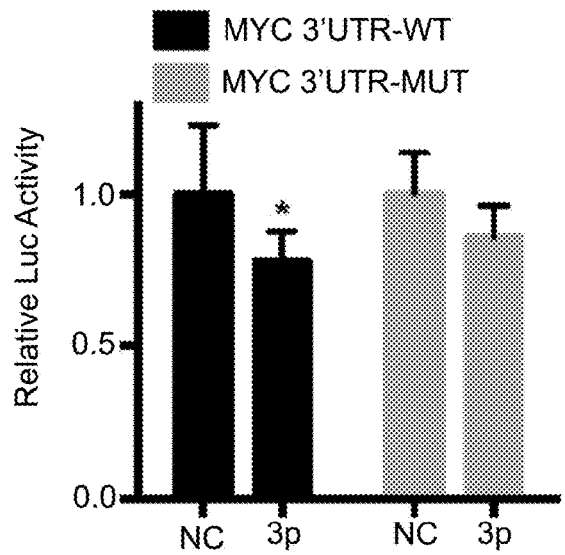
Figure 7D:
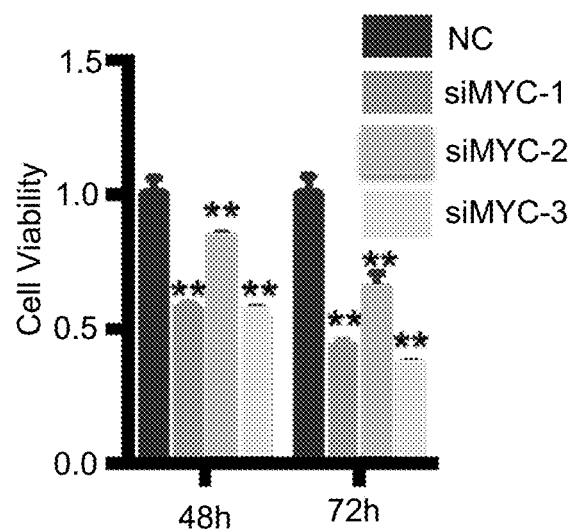
Figure 7E:
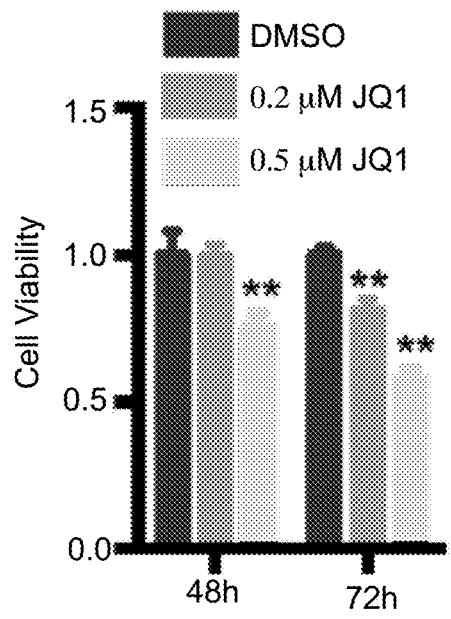
Figure 7F:
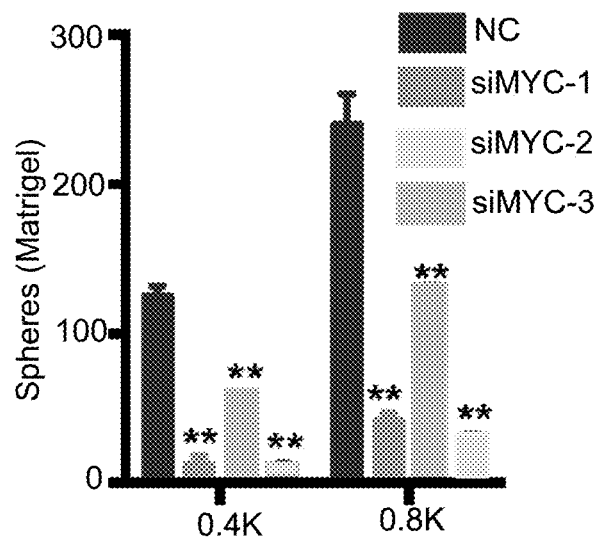

Further luciferase reporter assays confirmed that miR-199a-3p partially targeted c-Myc in PC3 cells (FIG. 7C). Consistent with c-Myc representing a functional downstream target of miR-199a-3p, knocking down endogenous c-Myc using 3 individual c-Myc-targeting siRNAs or inhibiting c-Myc expression using JQ1 (39) both inhibited PC3 cell viability (FIG. 7D-E). JQ1 and c-Myc siRNAs also inhibited clonogenic and sphere-forming capacities in PC3 cells, respectively (FIG. 7F). These results indicate that reduced expression of c-Myc facilitates the inhibitory effect of miR-199a-3p in prostate cancer cells such as PC3. Of note, either overexpression or knockdown of c-Myc had no effect on miR-199a-3p expression, although c-Myc was reported to modulate the expression of a number of microRNAs involved in the cell cycle and apoptosis (11,40).

Figure 7G:
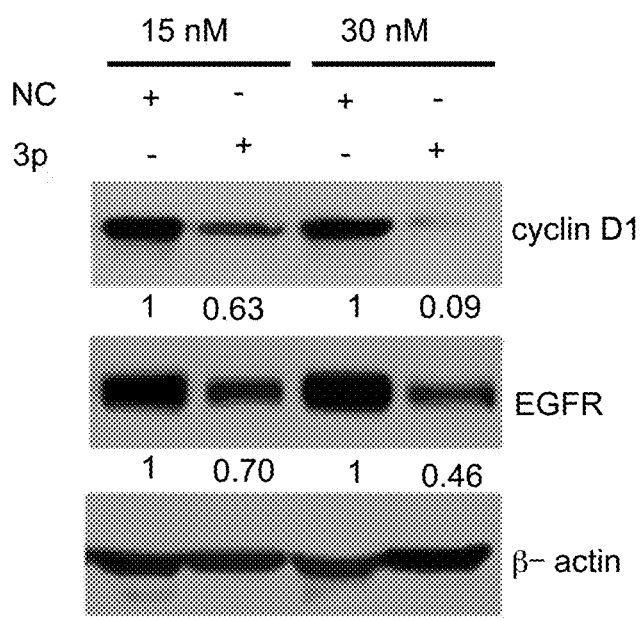
Figure 7H:
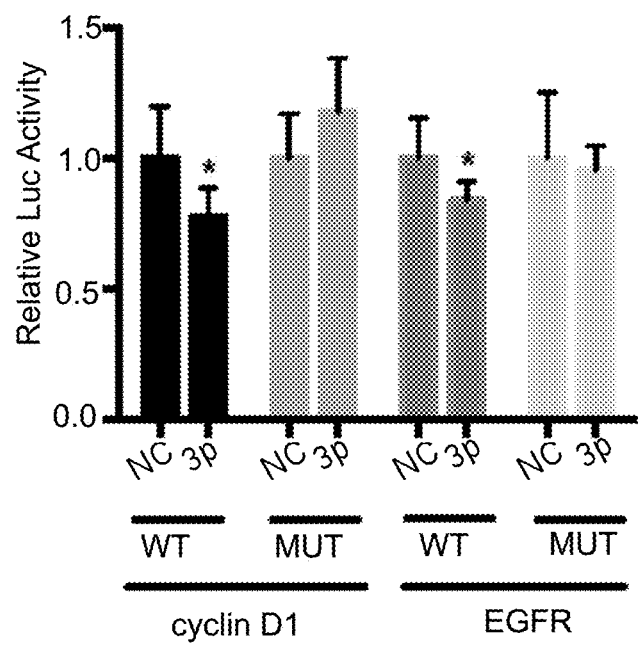
Figure 7I:
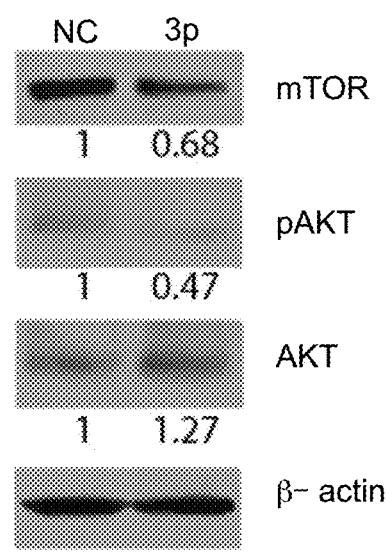

Collectively, these results suggest that c-Myc is regulated by miR-199a-3p in certain PCa cells. Similar to c-Myc, miR-199a-3p also reduced the protein levels of cyclin D1 and EGFR in PC3 cells (FIG. 7G). In silico analysis identified a putative miR-199a-3p binding site at the 3'-UTR of CCND1 (SEQ ID NO: 25) and EGFR (SEQ ID NO: 23), respectively (FIG. 7B). Luciferase reporter assays showed reduced luciferase activities in PC3 cells co-transfected with miR-199a-3p oligos and WT but not mutant cyclin D1 or EGFR 3'-UTR construct (FIG. 7H). These results indicate that miR-199a-3p regulates cyclin D1 and EGFR expression in PC3 cells. Finally, consistent with previous reports that miR-199a-3p also target other Oncogenic molecules such as mTOR (23,25), reduced mTOR protein levels were observed in DU145 cells transfected with miR-199a-3p oligos (FIG. 7I). Accompanying the mTOR reduction, pAKT was reduced without a decrease in the total AKT levels (FIG. 7I).

The present invention represents the very first comprehensive investigation on the biological functions of miR-199a-3p in prostate cancer. It is shown that overexpression of miR-199a-3p greatly inhibits proliferation and clonal and sphere-forming capacities of CD44+ as well as the bulk prostate cancer cells. Importantly, similar inhibitory effects have also been observed in primary patient tumor-derived HPCa cells. Impressively, miR-199a-3p expression inhibits both tumor initiation and tumor growth in several prostate cancer xenograft models. Preliminary studies have also revealed potential therapeutic efficacy of miR-199a-3p in retarding the growth of established xenograft tumors. Mechanistically, evidence are provided that like miR-34a, which is also under-expressed in CD44+ prostate cancer stem cells (9), miR-199a-3p directly targets CD44 in several prostate cancer cell types. The fact that 3 tumor-suppressive microRNAs, i.e., miR-34a (9), miR-708 (31), and miR-199a-3p (this study), simultaneously target 5 different sites at the CD44 3'-UTR (FIG. 6A), highlights the critical importance of CD44 in regulating cancer stem cell properties (6-10). Notably, present invention has provided evidence that miR-199a-3p may also exert tumor-suppressive functions via modulating several novel targets, i.e., c-Myc, cyclin D1, and EGFR. It seems that miR-199a-3p may target a different cohort of molecules in different prostate cancer cell types. For example, in PC3 cells it downregulates CD44, c-Myc, cyclin D1 and EGFR whereas in DU145 cells it targets CD44 and mTOR. Regardless, by simultaneously targeting a cohort of prooncogenic molecules, miR-199a-3p manifests powerful prostate cancer-suppressing effects, mainly through inhibiting cell proliferation. Altogether, results presented herein provide a rational for developing miR-199a-3p into anti-prostate cancer replacement therapeutics.

The following references are cited herein:
1. Kreso and Dick. *Cell Stem Cell* 2014; 14 (3):275-91.
2. Tang D G. *Cell Res* 2012; 22 (3):457-72.
3. Leung et al. *PLoS ONE* 2010; 5 (11):e14062.
4. Su et al. *EMBO J* 2011; 30 (15):3186-99.
5. Du et al. *Cancer Res* 2013; 73 (8):2682-94.
6. Patrawala et al. *Oncogene* 2006; 25 (12):1696-708.
7. Patrawala et al. *Cancer Res* 2007; 67 (14):6796-805.
8. Qin et al. *Cell Stem Cell* 2012; 10 (5):556-69.
9. Liu et al. *Nat Med* 2011; 17 (2):211-5.
10. Liu et al. *Oncotarget* 2015; 6 (27): 23959-86.
11. Ha and Kim. Nat Rev Mol Cell Biol 2014; 15 (8):509-24.
12. Ling et al. *Nat Rev Drug Discov* 2013; 12 (11):847-65.
13. Liu et al. *J Mammary Gland Biol Neoplasia* 2012; 17(1):15-21.
14. Liu and Tang. Cancer Res 2011; 71(18):5950-4.
15. Liu C et al. *Cancer Res* 2012; 72(13): 3393-404.
16. Hayes et al. *Trends Mol Med* 2014; 20(8):460-9.
17. Qu et al. *Am J Pathol* 2014; 184 (5):1541-9.
18. Li et al. *Methods Mol Biol* 2009; 568: 85-138.
19. Li et al. *Cancer Res* 2008; 68 (6):1820-5.
20. Jeter et al. *Stem Cells* 2009; 27 (5):993-1005.
21. Goldstein et al. *Nat Protoc* 2011; 6 (5):656-67.
22. Liu et al. *Cancer Lett* 2013; 329 (2):164-73.
23. Hou et al. *Cancer Cell* 2011; 19 (2):232-43.
24. Henry et al. *Biochem Biophys Res Commun* 2010; 403 (1):120-25.
25. Fornari et al. *Cancer Res* 2010; 70 (12):5184-93.
26. Kim et al. *J Biol Chem* 2008; 283 (26):18158-66.
27. Duan et al. *Mol Cancer Ther* 2011; 10 (8):1337-45.
28. Kinose et al. *Oncotarget* 2015; 6 (13):11342-56.
29. Minna et al. *Oncotarget* 2014; 5 (9):2513-28.
30. Goldstein et al. *Science* 2010; 329 (5991):568-71.
31. Saini et al. *Cancer Res* 2012; 72 (14):3618-30.
32. Dang C V. Cold Spring Harb Perspect Med 2013; 3(8).
33. Koh et al. *Genes Cancer* 2010; 1 (6):617-28.
34. Gil et al. *Cancer Res* 2005; 65(6):2179-85.
35. Civenni et al. *Cancer Res* 2013; 73 (22):6816-27.
36. Ding et al. *Nature* 2011; 470 (7333):269-73.
37. Ju et al. *Cancer Res* 2014; 74 (2):508-19.
38. Chang et al. *Cancer Res* 2015.
39. Asangani et al. *Nature* 2014; 510 (7504):278-82.
40. Chang et al. *Nat Genet* 2008; 40 (1):43-50.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. Also, the terms in the claims have their plain, ordinary meaning unless otherwise explicitly and clearly defined by the patentee.

What is claimed is:

1. A method of decreasing levels of c-Myc, cyclin D1, or EGFR in an individual having prostate cancer, comprising:
   administering to the individual a pharmacologically effective amount of a microRNA-199a oligonucleotide or microRNA-199a mimic that decreases a level of c-Myc, cyclin D1, or EGFR or a combination thereof in a prostate cancer stem cell.

2. The method of claim 1, wherein the microRNA-199a is miR-199a-3p, or miR-199a-5p.

3. The method of claim 2, wherein the miR-199a-3p has the sequence shown in SEQ ID NO: 22 or SEQ ID NO: 24.

4. The method of claim 1, wherein administering the microRNA-199a oligonucleotide or microRNA-199a mimic inhibits cell proliferation, invasion, migration, tumor growth, tumor regeneration, or metastatic potential or a combination thereof.

5. A method of inhibiting proliferation of a prostate cancer stem cell, comprising:
   contacting the prostate cancer stem cell with a pharmacologically effective amount of a microRNA-199a oligonucleotide or a microRNA-199a mimic that decreases a level of c-Myc, cyclin D1, or EGFR or a combination thereof in the prostate cancer stem cell.

6. The method of claim 5, wherein the microRNA-199a is miR-199a-3p or miR-199a-5p.

7. The method of claim 6, wherein the miR-199a-3p has the sequence shown in SEQ ID NO: 22 or SEQ ID NO: 24.

* * * * *

SEQUENCE LISTING

```
<160> NUMBER OF SEQ ID NOS: 26

<210> SEQ ID NO 1
<211> LENGTH: 851
<212> TYPE: DNA
<213> ORGANISM: Artificial Sequence
<220> FEATURE:
<223> OTHER INFORMATION: miR-199A1 sequence inserted into a lentiviral
      vector

<400> SEQUENCE: 1
cagctaatgc cacatctgga actgtttaca gtgcgattcc gccgagaaat            50
cagtggccgc cttcctggtg ctgccggcac gcacgcgtgc gcgcgcgcgc           100
acacacacac acacacgtgt gtgtgcgccc ctcctcccca cccccgaccc           150
ccaaagagtc agacattcct cctgagccca gaagccacga tcccaaaccc           200
tgcctcctgc tccgcctccc ccactctttta ggatttcctg aaaacccaga          250
actttctcca gatgcgagcc ggccccagcc ttgccacgtc agaagggaca           300
gagcggatcg tctcgggaag agtggtggtt tccttggctg ctcagaggtg           350
ctgaggcacg gcctggcctg gtggcccag cgtctgcctg ggggttctg             400 caggatggat agccggcccc gccaacccag tgttcagact acctgttcag           450
gaggctctca atgtgtacag tagtctgcac attggttagg ctgggcttgg           500
gtgagcggct cgtcgagaca ggccccccaa actcgccggc aggtgagtgt           550
cattttccac caccccgttt cccactgtgg cagagcctcg catagaagat           600
tcgagggcct gggtgggaga agaggcactg gggaaaggca gagggagccc           650
cgaggccggc cgagggttg gaggcctgg ccctatcagt ctgccatccc             700 cacccatgg ctgtaaatgt cttgtttatt ttttaaataa agagatattg            750
atgtcttgtg tctcactgag gcatctaaga gggtggcctc ctcctcaggg           800
gtggctgcca cgtgtgtgac tccaagggtc cctgctggga tcctaacttg          850
g                                                                851

<210> SEQ ID NO 2
<211> LENGTH: 24
<212> TYPE: DNA
<213> ORGANISM: Artificial Sequence
<220> FEATURE:
<223> OTHER INFORMATION: XhoI site of pGIPZ-199A

<400> SEQUENCE: 2
tactcgagca gctaatgcca catc                                       24

<210> SEQ ID NO 3
<211> LENGTH: 24
<212> TYPE: DNA
<213> ORGANISM: Artificial Sequence
<220> FEATURE:
<223> OTHER INFORMATION: MluI site of pGIPZ-199A

<400> SEQUENCE: 3
```
atacgcgtcc aagttaggat ccca                                              24

<210> SEQ ID NO 4
<211> LENGTH: 24
<212> TYPE: DNA
<213> ORGANISM: Artificial Sequence
<220> FEATURE:
<223> OTHER INFORMATION: ClaI site of lenti-199A

<400> SEQUENCE: 4
taatcgatca gctaatgcca catc                                              24

<210> SEQ ID NO 5
<211> LENGTH: 24
<212> TYPE: DNA
<213> ORGANISM: Artificial Sequence
<220> FEATURE:
<223> OTHER INFORMATION: MluI site of lenti-199A

<400> SEQUENCE: 5
atacgcgtcc aagttaggat ccca                                              24

<210> SEQ ID NO 6
<211> LENGTH: 26
<212> TYPE: DNA
<213> ORGANISM: Artificial Sequence
<220> FEATURE:
<223> OTHER INFORMATION: CD44 3' UTR-WT Forward Primer Sequence

<400> SEQUENCE: 6
agagctccac ctacaccatt atcttg                                            26

<210> SEQ ID NO 7
<211> LENGTH: 26
<212> TYPE: DNA
<213> ORGANISM: Artificial Sequence
<220> FEATURE:
<223> OTHER INFORMATION: CD44 3' UTR-WT Reverse Primer Sequence

<400> SEQUENCE: 7
taagcttgga agtcttcagg agacac                                            26

<210> SEQ ID NO 8
<211> LENGTH: 42
<212> TYPE: DNA
<213> ORGANISM: Artificial Sequence
<220> FEATURE:
<223> OTHER INFORMATION: CD44 3' UTR-MUT Forward Primer Sequence

<400> SEQUENCE: 8
cttaacagat gcaatgtgcc tgtcattgtt tcattgcgaa tc                          42

<210> SEQ ID NO 9
<211> LENGTH: 42
<212> TYPE: DNA
<213> ORGANISM: Artificial Sequence
<220> FEATURE:
<223> OTHER INFORMATION: CD44 3' UTR-MUT Reverse Primer Sequence

<400> SEQUENCE: 9
gattcgcaat gaaacaatga caggcacatt gcatctgtta ag                          42

<210> SEQ ID NO 10
<211> LENGTH: 208
<212> TYPE: DNA
<213> ORGANISM: Artificial Sequence
<220> FEATURE:
<223> OTHER INFORMATION: cyclin D1 3' UTR-WT Sequence

<400> SEQUENCE: 10

| | |
|---|---|
| taatctgtta tgtactagtg ttctgtttgt tattgttttg ttaattacac | 50 |
| cataatgcta atttaaagag actccaaatc tcaatgaagc cagctcacag | 100 |
| tgctgtgtgc cccggtcacc tagcaagctg ccgaaccaaa agaatttgca | 150 |
| ccccgctgcg ggcccacgtg gttggggccc tgccctggca gggtcatcct | 200 |
| gtgctcgg | 208 |

<210> SEQ ID NO 11
<211> LENGTH: 208
<212> TYPE: DNA
<213> ORGANISM: Artificial Sequence
<220> FEATURE:
<223> OTHER INFORMATION: cyclin D1 3' UTR-MUT Sequence

<400> SEQUENCE: 11

| | |
|---|---|
| taatctgtta tgtactagtg ttctgtttgt tattgttttg ttaattacac | 50 |
| cataatgcta atttaaagag actccaaatc tcaatgaagc cagctcacag | 100 |
| tcagctgtgc cccggtcacc tagcaagctg ccgaaccaaa agaatttgca | 150 |
| ccccgctgcg ggcccacgtg gttggggccc tgccctggca gggtcatcct | 200 |
| gtgctcgg | 208 |

<210> SEQ ID NO 12
<211> LENGTH: 207
<212> TYPE: DNA
<213> ORGANISM: Artificial Sequence
<220> FEATURE:
<223> OTHER INFORMATION: EGFR 3' UTR-WT Sequence

<400> SEQUENCE: 12

| | |
|---|---|
| acctcagacc gattaaacgc aaatctctgg ggctgaaacc caagcattcg | 50 |
| tagtttttaa agctcctgag gtcattccaa tgtgcggcca agttgagaa | 100 |
| ctactggcct agggattagc cacaaggaca tggacttgga ggcaaattct | 150 |
| gcaggtgtat gtgattctca ggcctagaga gctaagacac aaagacctcc | 200 |
| acatctg | 207 |

<210> SEQ ID NO 13
<211> LENGTH: 207
<212> TYPE: DNA
<213> ORGANISM: Artificial Sequence
<220> FEATURE:
<223> OTHER INFORMATION: EGFR 3' UTR-MUT Sequence

<400> SEQUENCE: 13

| | |
|---|---|
| acctcagacc gattaaacgc aaatctctgg ggctgaaacc caagcattcg | 50 |
| tagtttttaa agctcctgag gtcattccaa tgtgcggcca agttgagaa | 100 |
| atcccagcct agggattagc cacaaggaca tggacttgga ggcaaattct | 150 |
| gcaggtgtat gtgattctca ggcctagaga gctaagacac aaagacctcc | 200 |
| acatctg | 207 |

<210> SEQ ID NO 14
<211> LENGTH: 207
<212> TYPE: DNA

```
<213> ORGANISM: Artificial Sequence
<220> FEATURE:
<223> OTHER INFORMATION: MYC 3' UTR-WT Sequence

<400> SEQUENCE: 14
tgctccatga ggagacaccg cccaccacca gcagcgactc tgaggaggaa        50
caagaagatg aggaagaaat cgatgttgtt tctgtggaaa agaggcaggc       100
tcctggcaaa aggtcagagt ctggatcacc ttctgctgga ggccacagca       150
aacctcctca cagcccactg gtcctcaaga ggtgccacgt ctccacacat       200
cagcaca                                                      207

<210> SEQ ID NO 15
<211> LENGTH: 207
<212> TYPE: DNA
<213> ORGANISM: Artificial Sequence
<220> FEATURE:
<223> OTHER INFORMATION: MYC 3' UTR-MUT Sequence

<400> SEQUENCE: 15
tgctccatga ggagacaccg cccaccacca gcagcgactc tgaggaggaa        50
caagaagatg aggaagaaat cgatgttgtt tctgtggaaa agaggcaggc       100
gctctgcaaa aggtcagagt ctggatcacc ttctgctgga ggccacagca       150
aacctcctca cagcccactg gtcctcaaga ggtgccacgt ctccacacat       200
cagcaca                                                      207

<210> SEQ ID NO 16
<211> LENGTH: 35
<212> TYPE: DNA
<213> ORGANISM: Artificial Sequence
<220> FEATURE:
<223> OTHER INFORMATION: miR199A1 Sequence encoded from chromosome
      19p13.2

<400> SEQUENCE: 16
gccaacccag tgttcagact acctgttcag gaggc                        35

<210> SEQ ID NO 17
<211> LENGTH: 60
<212> TYPE: DNA
<213> ORGANISM: Artificial Sequence
<220> FEATURE:
<223> OTHER INFORMATION: miR199A2 Sequence encoded from chromosome
      1q24.3

<400> SEQUENCE: 17
aggaagcttc tggagatcct gctccgtcgc cccagtgttc agactacctg        50
ttcaggacaa                                                    60

<210> SEQ ID NO 18
<211> LENGTH: 36
<212> TYPE: DNA
<213> ORGANISM: Artificial Sequence
<220> FEATURE:
<223> OTHER INFORMATION: Chromosome 19p13.2 Sequence to encode
      miR-199a-3p

<400> SEQUENCE: 18
tctcaatgtg tacagtagtc tgcacattgg ttaggc                       36

<210> SEQ ID NO 19
```

```
<211> LENGTH: 50
<212> TYPE: DNA
<213> ORGANISM: Artificial Sequence
<220> FEATURE:
<223> OTHER INFORMATION: Chromosome 1q24.3 Sequence to encode
      miR-199a-3p

<400> SEQUENCE: 19
tgccgttgta cagtagtctg cacattggtt agactgggca agggagagca                50

<210> SEQ ID NO 20
<211> LENGTH: 22
<212> TYPE: RNA
<213> ORGANISM: Artificial Sequence
<220> FEATURE:
<223> OTHER INFORMATION: WT CD44 3' UTR Sequence

<400> SEQUENCE: 20
aacagaugca augugcuacu ga                                              22

<210> SEQ ID NO 21
<211> LENGTH: 22
<212> TYPE: RNA
<213> ORGANISM: Artificial Sequence
<220> FEATURE:
<223> OTHER INFORMATION: CD44 3' UTR MUT Sequence

<400> SEQUENCE: 21
aacagaugca augugccugu ca                                              22

<210> SEQ ID NO 22
<211> LENGTH: 22
<212> TYPE: RNA
<213> ORGANISM: Artificial Sequence
<220> FEATURE:
<223> OTHER INFORMATION: miR-199a-3p Sequence

<400> SEQUENCE: 22
acaguagucu gcacauuggu ua                                              22

<210> SEQ ID NO 23
<211> LENGTH: 22
<212> TYPE: DNA
<213> ORGANISM: Artificial Sequence
<220> FEATURE:
<223> OTHER INFORMATION: EGFR 3' UTR Sequence

<400> SEQUENCE: 23
cggccaaagt tgagaactac tg                                              22

<210> SEQ ID NO 24
<211> LENGTH: 22
<212> TYPE: DNA
<213> ORGANISM: Artificial Sequence
<220> FEATURE:
<223> OTHER INFORMATION: miR-199a-3p Sequence

<400> SEQUENCE: 24
acagtagtct gcacattggt ta                                              22

<210> SEQ ID NO 25
<211> LENGTH: 22
<212> TYPE: DNA
<213> ORGANISM: Artificial Sequence
<220> FEATURE:
<223> OTHER INFORMATION: CCND1 3' UTR Sequence
```

```
<400> SEQUENCE: 25
tgaagccagc tcacagtgct gt                                              22

<210> SEQ ID NO 26
<211> LENGTH: 22
<212> TYPE: DNA
<213> ORGANISM: Artificial Sequence
<220> FEATURE:
<223> OTHER INFORMATION: MYC 3' UTR Sequence

<400> SEQUENCE: 26
tggaaaagag gcaggctcct gg                                              22
```